(12) United States Patent
Lelkes et al.

(10) Patent No.: US 9,107,739 B2
(45) Date of Patent: Aug. 18, 2015

(54) SMALL DIAMETER VASCULAR GRAFT PRODUCED BY A HYBRID METHOD

(75) Inventors: Peter I. Lelkes, Cherry Hill, NJ (US); Mengyan Li, Tampa, FL (US); Anat Perets, Wynnewood, PA (US); Pimporn Uttayarat, Philadelphia, PA (US); Robert J. Levy, Merion Station, PA (US); Russell J. Composto, Philadelphia, PA (US)

(73) Assignees: Drexel University, Philadelphia, PA (US); The Children's Hospital of Philadelphia, Philadelphia, PA (US); The Trustees of the University of Pennsylvania, Philadelphia, PA (US)

( * ) Notice: Subject to any disclaimer, the term of this patent is extended or adjusted under 35 U.S.C. 154(b) by 195 days.

(21) Appl. No.: 13/511,511

(22) PCT Filed: Nov. 24, 2010

(86) PCT No.: PCT/US2010/058021
§ 371 (c)(1),
(2), (4) Date: Oct. 1, 2012

(87) PCT Pub. No.: WO2011/066401
PCT Pub. Date: Jun. 3, 2011

(65) Prior Publication Data
US 2013/0018454 A1  Jan. 17, 2013

Related U.S. Application Data

(60) Provisional application No. 61/264,573, filed on Nov. 25, 2009.

(51) Int. Cl.
*A61F 2/06* (2013.01)
*A61L 27/18* (2006.01)
(Continued)

(52) U.S. Cl.
CPC . *A61F 2/06* (2013.01); *A61L 27/18* (2013.01); *A61L 27/3808* (2013.01);
(Continued)

(58) Field of Classification Search
CPC ......... A61F 2/0007; A61F 2/04; A61F 2/062; A61F 2/0077
See application file for complete search history.

(56) References Cited

U.S. PATENT DOCUMENTS 5,833,641 A * 11/1998 Curtis et al. ............. 602/43
2002/0051806 A1 * 5/2002 Mallapragada et al. ...... 424/423
(Continued)

FOREIGN PATENT DOCUMENTS

WO    2009/094225 A2    7/2009

OTHER PUBLICATIONS

Courtney et al., "Design and analysis of tissue engineering scaffolds that mimic soft tissue mechanical anisotropy." 2006, Biomaterials 27(19):3631-3638.
Li et al., "Co-electrospun poly(lactide-co-glycolide), gelatin, and elastin blends for tissue engineering scaffolds." 2006, J Biomed Mater Res A, 79(4):963-73.
(Continued)

*Primary Examiner* — Jacqueline Woznicki
(74) *Attorney, Agent, or Firm* — Saul Ewing LLP; Kathryn Doyle

(57) ABSTRACT

The present invention relates to a hybrid graft and methods of generating the hybrid graft. The hybrid graft comprises an exterior surface and a luminal surface. The luminal surface comprises a micropattern of grooves to which cells adhere and orient along. The exterior surface comprises electrospun microfibers wherein the microfibers provide mechanical properties to the graft. The hybrid graft is capable supporting endothelial cell attachment, endothelial cell alignment, cell proliferation, and maintaining their in vivo function. The graft of the invention can recapitulate the in vivo morphology and function of natural vascular endothelium.

8 Claims, 9 Drawing Sheets

(51) Int. Cl.
  *A61L 27/38* (2006.01)
  *A61L 27/50* (2006.01)
  *D01D 5/00* (2006.01)
  *D01F 6/70* (2006.01)
  *A61F 2/00* (2006.01)

(52) U.S. Cl.
  CPC ........ *A61L 27/3813* (2013.01); *A61L 27/3817* (2013.01); *A61L 27/3821* (2013.01); *A61L 27/507* (2013.01); *D01D 5/0076* (2013.01); *D01F 6/70* (2013.01); *A61F 2/0077* (2013.01); *A61F 2/062* (2013.01); *A61F 2002/0081* (2013.01); *A61F 2002/0086* (2013.01); *A61F 2240/001* (2013.01); *A61F 2310/00005* (2013.01); *A61F 2310/00389* (2013.01); *A61L 2430/32* (2013.01)

(56) References Cited

U.S. PATENT DOCUMENTS

| | | |
|---|---|---|
| 2002/0086047 A1 | 7/2002 | Mueller et al. |
| 2004/0030377 A1 | 2/2004 | Dubson et al. |
| 2005/0239988 A1 | 10/2005 | Levy et al. |
| 2006/0085063 A1 | 4/2006 | Shastri et al. |
| 2008/0208316 A1 | 8/2008 | Shalev et al. |
| 2009/0028919 A1 | 1/2009 | Dancu |

OTHER PUBLICATIONS

Matsuda et al., "Mechano-active scaffold design of small-diameter artificial graft made of electrospun segmented polyurethane fabrics." 2005 J Biomed Mat Res 73: 125-31.
Sidouni et al., "Surface properties of a specifically modified high-grade medical polyurethane," 2001, Surface Science 491:355-369.
Stachelek et al., "Cholesterol-derivatized polyurethane: characterization and endothelial cell adhesion." 2005 J Biomed Mater Res A 72(2):200-12.
Stankus et al., "Fabrication of biodegradable elastomeric scaffolds with sub-micron morphologies." 2004, J Biomed Mater Res A. 70(4):603-14.
Stankus et al., "Microintegrating smooth muscle cells into a biodegradable, elastomeric fiber matrix." 2006, Biomaterials 27(5):735-44.
Uttayarat et al.,"Topographic guidance of endothelial cells on silicone surfaces with micro- to nanogrooves: Orientation of actin filaments and focal adhesions." 2005 J Biom Mat Res A 75(3):668-80.
Williamson et al., "PCL-PU composite vascular scaffold production for vascular tissue engineering: attachment, proliferation and bioactivity of human vascular endothelial cells." 2006 Biomaterials 27: 3608-16.
Zilla et al., "Prosthetic vascular grafts: wrong models, wrong questions and no healing." 2007 Biomaterials 28: 5009-27.
Extended European Search Report for EP Application No. 10833934.2 dated Jun. 12, 2014.

* cited by examiner

SMALL DIAMETER VASCULAR GRAFT PRODUCED BY A HYBRID METHOD

CROSS-REFERENCE TO RELATED APPLICATION

This application is the U.S. national phase application filed under 35 U.S.C. §371 claiming benefit to International Patent Application No. PCT/US2010/058021, filed on Nov. 24, 2010, which is entitled to priority under 35 U.S.C. §119(e) to U.S. Provisional Patent Application No. 61/264,573, filed on Nov. 25, 2009, each of which application is hereby incorporated herein by reference in its entirety.

BACKGROUND OF THE INVENTION

Current developments of artificial small diameter vascular grafts for patients with cardiovascular disease involves both material-based (Deutsch et al., 1999 Surgery 126: 847-55; Gulbins et al., 2006 Thorac Cardiovasc Surg 54: 102-7; Heydarkhan-Hagvall et al., 2006 Tissue Eng 12: 831-42; Ma et al., 2005 Tissue Eng 11: 1149-58; Matsuda et al., 2005 J Biomed Mat Res 73: 125-31; Williamson et al., 2006 Biomaterials 27: 3608-16; Zarge et al., 1997 J Surg Res 67: 4-8) and cell-based (Niklason et al., 1999 Science 284: 489-93; L'Heureux et al., 1998 FASEB 12: 47-56) approaches. The advantage of off-the-shelf avail able, ready-made grafts from synthetic polymers would favor a material-based approach, although the re-occurrence of thrombus formation and the lack of healing impede the long-term patency of such grafts, especially for those with small diameter (<4 mm) (Zilla et al., 2007 Biomaterials 28: 5009-27). These problems are often due to the mismatch in mechanical properties (Matsuda et al., 2005, J Biomed Mat Res 73: 125-31; Sarkar et al., 2006 Eur J Vasc Endovasc Surg. 31: 627-36) between synthetic grafts and native vascular vessels, as well as the absence of endothelial ingrowth in the midgraft area even after 10 years post surgery (Zilla et al., 2007 Biomaterials 28: 5009-27). Therefore, the fabrication of artificial grafts that possess elastic properties similar to those of native arteries and capable of facilitating endothelialization can significantly improve the healing of small-diameter grafts.

Current techniques of constructing 3-dimensional (3-D) synthetic vascular grafts include suturing a 2-D polymeric sheet into a 3-D tubular structure (Heydarkhan-Hagvall et al., 2006 Tissue Eng 12: 831-42) and electrospinning of polymer solution onto a rotating mandrel (Matsuda et al., 2005 J Biomed Mat Res 73: 125-31; Williamson et al., 2006 Biomaterials 27: 3608-16; Courtney et al., 2006 Biomaterials 27: 3631-8). Utilizing the electrospinning technique, various luminal surface topographies such as pores, non-woven mesh and oriented fibers can be created by adjusting the mandrel speed. Depending on the viscosity of polymer solution, electrospun fibers vary from nano- to micro-scale in diameter. In terms of mechanical property, the mesh morphology consisting of physically entangled fibers provide the mesh-type vascular scaffolds excellent compliance, compared to other structures, to withstand the pulsatile arterial flow (Matsuda et al., 2005 J Biomed Mat Res 73: 125-31).

Both porous (Zilla et al., 2007 Biomaterials 28: 5009-27) and mesh (Ma et al., 2005 Tissue Eng 11: 1149-58) topographies have been shown to promote capillary ingrowth, spreading, adhesion, mid proliferation of endothelial cells. Oriented-fiber topography guides endothelial cell alignment, similar to the groove-like topography that induces the alignment of many cell types (Oakley et al., 1995 Cell Motil Cytoskeleton 31: 45-58; Jiang et al., 2002 Langmuir 18: 3273-3280; den Braber et al., 1996 Biomaterials 17; 2037-44; den Braber et al., 1998 J Biomed Mater Res 40: 291-300; Uttayarat et al., 2005 J Biomed Mater Res 75: 668-80). This alignment of endothelial monolayer emulates the naturally aligned and elongated endothelium in linear vascular vessels under hemodynamic flow environment (Uttayarat et al., 2005 J Biomed Mater Res 75: 668-80; Nerem et al., 1981 J Biomech Eng 103: 172-6) and also guides directional cell migration (Uttayarat et al., 2008, Am J Physiol Heart Circ Physiol. 294:1-H1027-35). A recent fabrication of synthetic graft combines both mesh and oriented fiber morphology as demonstrated in the polycaprolactone-polyurethane (PCL-PU) composite vascular graft (Williamson et al., 2006 Biomaterials 27: 3608-16), where the lumen exhibits oriented PCL microfibers and the exterior comprises highly porous PU (about 10 to 30 μm in diameter).

Electrospinning was developed in the textile industry in the 1930s (Bergshoef et al., 1999 Adv Mater 11: 1362-1365; Huang et al., 2003 Composites Sci Technol 63: 2223-2253; Jin et al. 2002 Biomacromolecules 3: 1233-1239) and has recently been applied to tissue engineering as a versatile platform technology for generating biomimetic fibrous scaffolds to be used as grafts such as synthetic vascular vessels (Drasler et al., 1993 ASAIO J 39: 114-119; Ma et al., 2005 Tissue Eng 11: 1149-58; Matsuda et al., 2005 J Biomed Mat Res 73: 125-31; Vaz et al., 2005 Acta Biomater 1: 575-582; Williamson et al., 2006 Biomaterials 27: 3608-16), cardiac patches (Hidalgo-Bastida et al., 2007 Acta Biomater 3: 457-462; Stankus et al., 2006 Biomaterials 27:735-744) and wound dressing (Chong et al., 2007 Acta Biomater 3: 32) -330; Khil et al., 2003 J Biomed Mater Res B Appl Biomater 67: 675-679; Rho et al., 2006 Biomaterials 27: 1452-61; Zhou et al., 2008 Biomacromolecules 9: 349-354). During the electrospinning process, the fiber size, fiber density as well as fiber organization can be modulated, thus enabling tight control over the scaffold structure. This complexity of the electrospun scaffolds emulates several features of natural extracellular matrix (ECM), which possesses pores and topographic cues for cell adhesion and proliferation (Li et al., 2006 J Biomed Mater Res A, 79: 963-73; Ma et al., 2005 Tissue Eng 11: 1149-58). Previous studies on synthetic vascular vessels made from Dacron or Goretex (Zilla et al, 2007 Biomaterials 28: 5009-27) have shown transmural ingrowth of capillaries through micro-scale pores in the vessel walls thus allowing the migration of vascular endothelial cells to cover the synthetic surface, in addition, for gratis embedded with directionally oriented microfibers, endothelial cells aligned their cell shape parallel to the fiber direction (Ma et al., 2005 Tissue Eng 11: 1149-58), similar to the flow-induced cell alignment observed in vivo (Nerem et al., 1981 J Biomech Eng 103: 172-6).

Polyurethane (PU) is preferred over traditional materials, such as Dacron and Cortex, for the fabrication of cardiovascular prostheses (Sarkar et al., 2006 Eur J Vasc Endovasc Surg. 31: 627-36; Tiwari et al., 2002 Cardiovasc Surg. 10; 191-7). Recently, polyurethane has been incorporated in the electrospinning process to fabricate synthetic vascular vessels (Ma et al., 2005 Tissue Eng 11: 1149-58; Matsuda et al., 2005 J Biomed Mat Res 73: 125-31; Williamson et al., 2006 Biomaterials 27: 3608-16) as well as heart leaflets (Courtney et al., 2006 Biomaterials 27: 3631-3638). For example, Courtney et al showed that poly(ester urethane) ureas electrospun onto a rotating mandrel exhibited anisotropic compliance, in which the scaffold is stiffer when stretched in the direction of aligned fibers compared to when stretch in the orthogonal direction to fibers. This anisotropic mechanical property strongly resembles the native pulmonary valve leaflet, as it requires almost 150% more stretch in the radial direction than in the circumferential direction to achieve the same membrane tension (Courtney et al., 2006 Biomaterials 27: 3631-3638). Concomitantly, the innate mechanical property of PU, the organization of electrospun PU fibers endows the scaffold with anisotropic compliance to closely mimic some of the more intricate mechanical properties of natural vascular tissues.

Angiogenesis is the formation of new blood vessels from established vascular beds. This complex process involves the migration and proliferation of existing vascular endothelial cells (EC), the formation of immature EC tubules, and maturation stages in which mesenchymal cells are recruited and differentiate into the pericytes or smooth muscle cells of the outer vessel layers (Risau, 1997 Nature 386: 671-674; Hanahan, 1997 Science 277: 48-50; Jain et al., 1997 Nature Medicine 3: 1203-1208).

Endothelial cells promote healing of damaged blood vessels within the body by promoting angiogenesis. In addition, endothelial cells can inhibit platelet adhesion and thrombus formation on blood-contacting surfaces.

Despite advances in tissue engineering, current three-dimensional vascular grafts generally lack structure sufficient to achieve adequate cell attachment and endothelialization to recapitulate natural endothelium. Accordingly, there remains a need for three-dimensional vascular grafts having suitable properties such as being able to support endothelial cell attachment, endothelial cell alignment, cell proliferation, and maintaining endothelial cell function in vivo. The invention fulfills this need.

SUMMARY OF THE INVENTION

The present invention includes a hybrid graft comprising an exterior surface and a luminal surface. Preferably, the luminal surface comprises a micropattern of grooves to which cells adhere and orient along, and wherein the exterior surface comprises electrospun microfibers wherein the microfibers provide mechanical properties to the graft.

In one embodiment, the hybrid graft is produced using a hybrid method, wherein the method comprises the combination of a first electrocasting/electrospraying methodology to produce a micropatterned surface on the luminal surface and a second electrospinning methodology to produce electrospun fibers on the exterior surface.

In one embodiment, each groove has a depth of about 1 µm and a width of about 5 µm, and each groove is positioned 5 µm apart from each other.

In one embodiment, the cells are selected from the group consisting of chondroblasts, chondrocytes, fibroblasts, endothelial cells, osteoblasts, osteocytes, epithelial cells, epidermal cells, mesenchymal cells, hemopoietic cells, nerve cells, Schwann cells, glial cells, stem cells, dorsal root ganglia, and combinations thereof.

In one embodiment, the graft is a vascular graft.

In one embodiment, the luminal surface comprises a polymeric material selected from the group consisting of poly-(D, L-lactide-co-glyeolide) (PLGA), poly-(dimethylsiloxane) (PDMS), poly-(L-lactide-co-caprolactone-co-glycolide) (PLCG), polycaprolactone (PCL), polylactic acid (PLA), polystyrene, polyurethane, polytetrafluoroethylene (ePTFE), and tetraphthlate (Dacron).

In one embodiment, the luminal surface comprises cholesterol modified polyurethane.

In one embodiment, the luminal surface and exterior surface comprise cholesterol modified polyurethane.

In one embodiment, the graft promotes endothelialization and is non-thrombogenic.

The invention it hides a method of making a hybrid graft. The method comprising generating a micropatterned luminal surface by electrocasting/electrospraying a first elastomeric polymer on a micropatterned mandrel thereby generating a casted graft, followed by electrospinning a second elastomeric polymer on the casted graft to produce electrospun fibers on the exterior surface of the graft.

In one embodiment, the first elastomeric polymer and second elastomeric polymer is cholesterol modified polyurethane.

In one embodiment, the micropattern luminal surface comprises grooves to which cells adhere and orient along, wherein each groove has a depth of about 1 µm and a width of about 5 µm, and each groove is positioned 5 µm apart from each other.

The invention provides a method of making a synthetic tubular graft. In one embodiment, the method comprising generating a micropatterned luminal surface by electrocasting/electrospraying a first elastomeric polymer on a micropatterned mandrel thereby generating a casted graft, followed by electrospinning it second elastomeric polymer on the casted graft to produce electrospun fibers on the exterior surface of the graft.

In one embodiment, the first elastomeric polymer and second elastomeric polymer is cholesterol modified polyurethane.

In one embodiment, the micropattern luminal surface comprises grooves to which cells adhere and orient along, wherein each groove has a depth of about 1 µm and a width of about 5 µm, and each groove is positioned 5 µm apart from each other.

The invention includes a method of treating a vascular disease in a mammal. In one embodiment, the method comprising implanting a hybrid graft comprising an exterior surface and a luminal surface in mammal in need thereof, wherein the luminal surface comprises a micropattern of grooves to which cells adhere and orient along, and wherein the exterior surface comprises electrospun microfibers.

The invention also includes a guidance channel for promoting nerve regeneration comprising a hybrid graft comprising an exterior surface and a luminal surface, wherein the luminal surface comprises a micropattern of grooves to which cells adhere and orient along, and wherein the exterior surface comprises electrospun microfibers wherein the microfibers provide mechanical properties to the graft.

In one embodiment, the graft comprises a first end for connection to a proximal stump of a severed nerve and a second end for connection to a distal stump of the severed nerve.

The invention includes a method of promoting nerve regeneration between severed stumps of a nerve. In one embodiment, the method comprises providing a nerve guidance channel comprising a hybrid graft comprising an exterior surface and a luminal surface, wherein the luminal surface comprises a micropattern of grooves to which cells adhere and orient along, and wherein the exterior surface comprises electrospun microfibers wherein the microfibers provide mechanical properties to the graft, further wherein said graft comprises first and second ends; connecting the proximal stump of the nerve to the first end of the guidance channel; and connecting the distal stump of the nerve to the second end of the guidance channel whereby nerve regeneration occurs on the luminal surface of the graft.

BRIEF DESCRIPTION OF THE DRAWINGS

For the purpose of illustrating the invention, there are depicted in the drawings certain embodiments of the invention. However, the invention is not limited to the precise arrangements and instrumentalities of the embodiments depicted in the drawings.

FIGS. 1A and 1B, is a series of images depicting a representative small caliber polyurethane graft fabricated by electrospinning methodology. FIG. 1A depicts a graft diameter of 4 mm and FIG. 1B depicts a graft length of 4.5 cm.

FIGS. 2A through 2F, is a series of scanning electron images of polyurethane grafts having micro-scale topographies on the graft lumens. Using electrospinning technique with mandrel rotating at 3000 rpm (FIGS. 2A and 2B), microfibers with diameter of 1.2 (±0.3) μm aligned helically along the graft length. FIGS. 2C and 2D demonstrate that microchannels were uniformly textured on the lumen of polyurethane graft using spin casting technique. The ridge width, channel width, and channel depth were 3.6 (±0.2), 3.9 (±0.1) and 0.9 (±0.03) μm, respectively. FIGS. 2E and 2F demonstrate that the combination of spin casting and electrospinning techniques with mandrel rotation speed set at 50 rpm yielded a graft with microchannels on the lumen and mesh of microfibers on the exterior.

FIGS. 3A through 3C, is a series of images demonstrating formation of an endothelial monolayer on spun cast grafts having microchannels on the lumen as visualized by immunostaining for endothelial phenotypic marker VE-cadherin (green) (FIGS. 3A and 3B) and scanning electron microscopy (SEM) (FIG. 3C). Both human umbilical derived EA.hy926 endothelial cells (FIG. 3A) and bovine aortic endothelial cells (BAECs) (FIG. 3B) showed intense VE-cadherin staining at cell-cell contacts, which outlined the elongated cell shape parallel to the channel direction (dashed lines). Dashed lines guide the direction of channels. A slight trace of channels under cells are visible in both images. Arrows point at nuclei situated over a ridge and a channel. Scale bar is 50 μm for both images. SEM image of as BAEC monolayer with cell alignment parallel to channels (FIG. 3C).

FIGS. 4A through 4C, is a series fluorescence and scanning electron microscopy (SEM) images of an endothelial monolayer formed on the lumen of electrospun grafts after seven days in culture. Actin microfilaments and nuclei are in red and blue, respectively. Bovine aortic, (FIG. 4A) and human umbilical vein-derived EA.hy926 endothelial cells (FIG. 4B) maintained their alignment parallel to the fiber direction at confluence. Dashed lines guide the direction of microfibers. Scale bar is 50 μm for both images. SEM image confirmed the uniform coverage of cells on the graft lumen as demonstrated in the EA.hy926 monolayer (FIG. 4C). The alignment of cell shape also followed the fiber direction shown by dashed line.

FIGS. 5A and 5B, is a series of images depicting TNF-α induced ICAM-1 expression of EA.hy926 endothelial cells grown on artificial polyurethane surfaces.

FIGS. 6A through 6I, is a series of images depicting morphology of electrospun PU microfibers visualized by SEM. In DMF-based solutions, microfibers exhibited irregular clumps along the fiber length at 7% (w/v) PU concentration (FIG. 6A), whereas small kinks remain on the fiber at higher PU concentrations, 8.5% (w/v) (FIG. 6B) and 10% (w/v) (FIG. 6C). In THF-based solutions, bead-shape clumps formed at 7% and 8.5% (w/v) PU concentrations as shown in (FIG. 6D) and (FIG. 6E), respectively, and disappeared at the highest concentration of 10% (w/v) (FIG. 6F). For PU solutions prepared in HIT, clumps were observed at 1% (w/v) concentration (FIG. 6G). At 3% (w/v) concentration (H), microfibers became smooth and formed an interconnected network. FIG. 6I is an image showing that at 5% (w/v) concentration, a woven mesh of smooth microfibers was observed, similar to the pattern observed in FIG. 6F.

FIGS. 7A through 7E, depicts a representative small diameter electrospun PU graft. The length (FIG. 7A) and diameter (FIG. 7B) of graft fabricated from HFP-based solution are 28 mm and 4 mm, respectively. Inspected by SEM, graft prepared from DMF-based solution (FIG. 7C) exhibited rough surface morphology without the formation of microfibers on the lumen. Microfibers were observed on the lumen of grafts prepared from 10% (w/v) PU in THE (FIG. 7D) as well as 5% (w/v) PU in HFP (FIG. 7E). The helical alignment of microfibers was present only in a graft prepared from HFP-based solution.

FIGS. 8A through 8C, depicts realignment of electrospun PU microfibers after tensile testing. Different mechanical behaviors were observed in PU mesh and PU graft fabricated from HFP-based solution under tensile load (FIG. 8A). SEM images show the organization of microfibers after the application of tensile stress (FIG. 8B) parallel to the graft's longitudinal direction (north-south axis) and (FIG. 8C) transverse to the graft. Open arrow heads point at randomly oriented microfibers or those that are in the process of realigning in the load direction, whereas solid arrow head indicates a few fibers that maintain their alignment transverse to the load (FIG. 8B). Microfibers form bundles and maintain their alignment with the load direction as indicated by solid arrows (FIG. 8C).

FIGS. 9A through 9E, is a series of images depicting cell proliferation and cell orientation on electrospun PU scaffolds. Fluorescent staining of actin microfilaments and nuclei are shown in red and blue, respectively. For PU mesh geometry, EA.Hy926 proliferated and formed a monolayer on all mesh PU samples prepared from DMF (FIG. 9A), THF (FIG. 9B) and HFP (FIG. 9C) solutions. Scale bar is 50 μm for images depicting in Figures FIG. 9A-9C. For PU graft, EA.Hy926 monolayer formed on both lumen and exterior of the graft (FIG. 9D). At confluence, cells maintained their alignment parallel to the helically oriented microfibers (FIG. 9E) guided by dashed line. Scale bars are 5 mm and 50 μm in FIG. 9D and FIG. 9E, respectively.

DETAILED DESCRIPTION OF THE INVENTION

Figure 1:
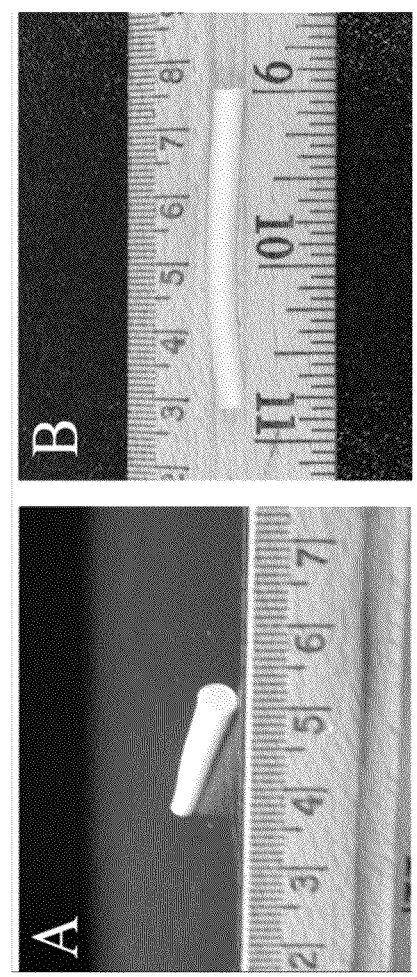
FIG. 1 comprising

The present invention is based a at the successful fabrication of a functional micropatterned 3-dimensional (3-D) vascular graft that is capable of supporting endothelial cell attachment, endothelial cell alignment, cell proliferation, and maintaining endothelial cell function in vivo. The graft of the invention can recapitulate the in viva morphology and function of natural vascular endothelium. The ability of the graft to induce endothelialization provides a method to recapitulate natural endothelium and promote in vivo healing after implantation of the graft in a mammal in need thereof.

The graft of the invention is produced using a hybrid methodology comprising the use of electrospinning and spin casting techniques to generate a small diameter graft having a micropatterned luminal surface that exhibits desirable mechanical and biocompatible properties. Preferably, the hybrid graft of the invention has a small diameter of about 4 mm. The hybrid graft is constructed by electrospinning and spin casting techniques to create uniform microfibers and micro channels on the lumen. The combination of both techniques produces a hybrid graft, which exhibits microchannels on the lumen and mesh of electrospun microfibers on the exterior of the graft. The graft of the invention is a new generation of multifunctional synthetic graft.

One aspect of the invention is a hybrid graft comprising on the lumen, a surface micropatterned with parallel grooves to which endothelial cells adhere to and orient along. Each groove is about 1 to 20 μm wide and the distance between each groove is about 1 to 20 μm. Each groove has a depth of about 1 to 5 μm. In a preferred embodiment, each groove has a depth of 1 μm, a width of 5 μm, and a distance between each groove of 5 μm.

The invention provides a hybrid method to produce is hybrid graft that combines a first methodology (e.g., electrocasting/electrospraying) for generating precisely controlled micropatterned surfaces with a second method (e.g., electrospinning) for generating compliant vascular grafts with precise control of their mechanical/elastic properties. Preferably, the hybrid method comprises generating a thin micropatterned luminal surface by electrocasting mid for electrospraying a suitable elastomeric polymer (e.g., polyurethane) onto a micropatterned mandrel, followed by electrospinning of the same or another material, which provides the necessary compliance and mechanical properties of the entire graft. However, in some instance, the invention includes the use of a suitable inelastomeric polymer.

The invention is also related to the discovery that vascular tissue can be generated hi vivo. The hybrid graft of the invention is able to recapitulate natural endothelium and promote in vivo healing after implantation of the graft. Accordingly, the invention provides methods and compositions for the generation of vascular tissues as a form of regenerative medicine.

The invention also provides a method of alleviating or treating a vascular detect in a mammal, preferably a human. The method comprises administering to the mammal in need thereof a therapeutically effective amount of a composition comprising a hybrid graft of the invention, thereby alleviating or treating the lung defect in the mammal.

DEFINITIONS

Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, organic chemistry, and nucleic acid chemistry and hybridization are those well known and commonly employed in the art.

Standard techniques are used for nucleic acid and peptide synthesis. The techniques and procedures are generally performed according to conventional methods in the art and various general references (e.g., Sambrook and Russell, 2001, Molecular Cloning, A Laboratory Approach, Cold Spring Harbor Laboratory Press, Cold Spring Harbor, N.Y., and Ausubel et al., 2002, Current Protocols in Molecular Biology, John Wiley & Sons, New York, N.Y.), which are provided throughout this document.

The articles "a" and "an" are used herein to refer to one or to more than one (i.e., to at least one) of the grammatical object of the article. By way of example, "an element" means one element or more than one element.

The term "about" will be understood by persons of ordinary skill in is art and will vary to some extent based on the context in which it is used.

As used herein, to "alleviate" a disease, defect, disorder or condition means reducing the severity of one or more symptoms of the disease, defect, disorder or condition.

"Angiogenesis" as used herein, refers to the formation of new blood vessels.

As used here, "biocompatible" refers to any material, which, when implanted in a mammal, does not provoke an adverse response in the mammal. A biocompatible material, when introduced into an individual, is not toxic or injurious to that individual, nor does it induce immunological rejection of the material in the mammal.

"Differentiation medium" is used herein to refer to a cell growth medium comprising an additive or a lack of an additive such that a stem cell or progenitor cell, that is not fully differentiated, develops into a cell with some or all of the characteristics of a differentiated cell when incubated in the medium.

The term "electroprocessing" as used herein shall be defined broadly to include all methods of electrospinning, electrospraying, electroaerosoling, and electrosputtering of materials, combinations of two or more such methods, and any other method wherein materials are streamed, sprayed, sputtered or dripped across an electric field and toward a target. The electroprocessed material can be electroprocessed from one or more grounded reservoirs in the direction of a charged substrate or from charged reservoirs toward a grounded target, "Electrospinning" means a process in which fibers are formed him a solution or melt by streaming an electrically charged solution or melt through an orifice. "Electroaerosoling" means a process in which droplets are formed from a solution or melt by streaming an electrically charged polymer solution or melt through an orifice. The term electroprocessing is not limited to the specific examples set forth herein, and it includes any means of using an electrical field for depositing a material on a target.

As used herein "endogenous" refers to any material from or produced inside an organism, cell or system.

"Exogenous" reels to any material introduced into or produced outside an organism, cell, or system.

As used herein, "epithelial cell" means a cell which forms the outer surface of the body and lines organs, cavities and mucosal surfaces.

As used herein, "endothelial cell" means a cell which lines the blood and lymphatic vessels and various other body cavities.

As used herein, a "substantially purified" cell is a cell that is essentially free of other cell types. Thus, a substantially purified cell refers to a cell which has been purified from other cell types with which it is normally associated in its naturally-occurring state.

"Expandability" is used herein to refer to the capacity of a cell to proliferate, for example, to expand in number or, in the case of a population of cells, to undergo population doublings.

As used herein, a "graft" refers to a cell, tissue, organ, scaffold, and the like that is implanted into an individual, typically to replace, correct or otherwise overcome a defect. The graft may comprise of cells that originate from the same individual: this graft is referred to herein by the following interchangeable terms: "autograft", "autologous transplant", "autologous implant" and "autologous graft". A graft comprising cells from a genetically different individual of the same species is referred to herein by the following interchangeable terms: "allograft", "allogeneic transplant", "allogeneic implant" and "allogeneic graft". A graft from an individual to his identical twin is referred to herein as an "isograft", a "syngeneic transplant", a "syngeneic implant" or a "syngeneic graft". A "xenograft", "xenogeneic transplant" or "xenogeneic implant" refers to a graft from one individual to another of a different species.

"Hybrid graft" as used herein refers to a three-dimensional (3-D), micropatterned grafts that possess mechanical property of natural artery, promote cell alignment, and enable the cells to maintain their in vivo functions. Hybrid grafts of the invention are constructed using the hybrid methods of the invention (e.g., electrospinning and spin casting techniques) to create uniform microfibers and microchannels on the lumen. The hybrid grafts exhibit microchannels on the lumen and mesh of electrospun microfibers on the exterior.

As used herein, the term "growth medium" is meant to refer to a culture medium that promotes growth of cells. A growth medium will generally contain animal serum, in some instances, the growth medium may not contain animal serum.

As used herein, the term "growth factor product" refers to a protein, peptide, mitogen, or other molecule having a growth, proliferative, differentiative, or trophic effect on a cell, Growth factors include, but are not limited to, fibroblast growth factor (FGF), basic fibroblast growth factor (bFGF), acidic fibroblast growth factor (aFGF), epidermal growth factor (EGF), insulin-like growth factor-1 (IGF-T), insulin-like growth factor-II (IGF-II), platelet-derived growth factor (PDGF), vascular endothelial cell growth factor (VEGF), activin-A, bone morphogenic proteins (BMPs), insulin, growth hormone, erythropoietin, thrombopoietin, interleukin 3 (IL-3), interleukin 6 (IL-6), interleukin 7 (IL-7), macrophage colony stimulating factor, c-kit ligand/stein cell factor, osteoprotegerin ligand, insulin, nerve growth factor, ciliary neurotrophic factor, cytokines, chemokines, morphogens, neutralizing antibodies, other proteins, and small molecules. Preferably, the FGF is selected from the group selected from FGF2, FGF7, FGF10, and any combination thereof.

An "isolated cell" refers to a cell which has been separated from other components and/or cells which naturally accompany the isolated cell in a tissue or mammal.

The term "patient" as used herein includes human and veterinary subjects.

The term "polyurethane," as used herein, is a polymer that comprises repeating units having a urethane group in the polymer backbone. Such polymers include, for example, polyurethane homopolymers, block co-polymers comprising at least one polyurethane block, and polymer blends comprising such homopolymers and block co-polymers.

The terms "precursor cell," "progenitor cell," and "stem cell" are used interchangeably in the art and as used herein refer either to a pluripotent or lineage-uncommitted progenitor cell, which is potentially capable of an unlimited number of mitotic divisions to either renew itself or to produce progeny cells which will differentiate into the desired cell type, in contrast to pluripotent stem cells, lineage-committed progenitor cells are generally considered to be incapable of giving rise to numerous cell types that phenotypically differ from each other, instead, progenitor cells give rise to one or possibly two lineage-committed cell types.

"Proliferation" is used herein to refer to the reproduction or multiplication of similar forms, especially of cells. That is, proliferation encompasses production of a greater number of cells, and can be measured by, among other things, simply counting the numbers of cells, measuring incorporation of $^3$H-thymidine into the cell, and the like.

As used herein, "scaffold" refers to a structure, comprising a biocompatible material, that provides a surface suitable for adherence and proliferation of cells. A scaffold may further provide mechanical stability and support. A scaffold may be in a particular shape or form so as to influence or delimit a three-dimensional shape or form assumed by a population of proliferating cells. Such shapes or forms include, but are not limited to, films (e.g. a firm with two-dimensions substantially greater than the third dimension), ribbons, cords, sheets, flat discs, cylinders, spheres, 3-dimensional amorphous shapes, etc.

As used herein, the term "solution" is used to describe the liquid in the reservoirs of the electroprocessing method. The term is defined broadly to include any liquids that contain materials to be electroprocessed. It is to be understood that any solutions capable of forming a material during electroprocessing are included within the scope of the present invention. "Solutions" can be in organic or biologically compatible forms. This broad definition is appropriate in view of the large number of solvents or other liquids (polar and non-polar) and carrier molecules that can be used in the many variations of electroprocessing.

As used herein, the terms "tissue grafting" and "tissue reconstructing" both refer to implanting a graft into an individual to treat or alleviate a tissue defect, such as a vascular defect or a soft tissue defect.

As used herein, "tissue engineering" refers to the process of generating tissues ex vivo for use in tissue replacement or reconstruction. Tissue engineering is an example of "regenerative medicine," which encompasses approaches to the repair or replacement of tissues and organs by incorporation of cells, gene or other biological building blocks, along with bioengineered materials and technologies.

As used herein, to "treat" means reducing the frequency with which symptoms of a disease, defect, disorder, or adverse condition, and the like, are experienced by a patient.

As used herein, a "therapeutically effective amount" is the amount of a composition of the invention sufficient to provide a beneficial effect to the individual to whom the composition is administered.

"Three-dimensional cell culture" or "3-D cell culture" as used herein, refers to cell cultures wherein cell expansion can occur in any direction as long as the cells are not at the edge of the culture.

"Tissue cell culture" as used herein refers to an aggregation of cells and intercellular matter performing one or more functions in an organism. Examples of tissues include, but are not limited to, epithelium, connective tissues (e.g., bone, blood, cartilage), muscle tissue and nerve tissue.

"Two-dimensional cell culture" or "2-D cell culture" as used herein, refers to conventional monolayer cell culture. Generally, every cell in a 2-D culture directly contacts the substratum on the plate and the cultures, therefore, only expand horizontally as they proliferate.

The term "vascular" as used herein means related to blood vessels. Preferably, the blood vessels are part of the circulatory system. For example, an organ or tissue that is vascularized is heavily endowed with blood vessels and thereby richly supplied with blood.

"Vascularization" as used herein, refers to the formation of new blood vessels or growth of existing vessels for perfusing tissues.

"Vascular remodeling" as used herein, refers to the maturation of endothelial cell tubules into complex endothelium-lined microvessels invested with mesenchymal cells such as pericytes and smooth muscle cells. The presence of the smooth muscle cells can be determined by measuring smooth muscle actin expression.

The term "vascular specific" refers to a nucleic acid molecule or polypeptide that is expressed predominantly in tissues related to blood vessels as compared to other tissues in the body. In a preferred embodiment, a "vascular specific" nucleic acid molecule or polypeptide is expressed at a level that is 5-fold higher than any other tissue in the body. In a more preferred embodiment, the "vascular specific" nucleic acid molecule or polypeptide is expressed at a level that is 10-fold higher than any other tissue in the body, more preferably at least 15-fold, 20-fold, 25-fold, 50-fold or 100-fold higher than any other tissue in the body. Nucleic acid molecule levels may be measured by nucleic acid hybridization, such as Northern blot hybridization, or quantitative PCR. Polypeptide levels may be measured by any method known to accurately measure protein levels, such as Western blot analysis.

Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, as gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

An "isolated nucleic acid" refers to a nucleic acid segment or fragment which has been separated from sequences which flank it in a naturally-occurring state, i.e., a DNA fragment which has been removed from the sequences which are normally adjacent to the fragment, i.e., the sequences adjacent to the fragment in a genome in which it naturally occurs. The term also applies to nucleic acids which have been substantially purified from other components which naturally accompany the nucleic acid, i.e., RNA or DNA or proteins, which naturally accompany it in the cell. The term therefore includes, for example, a recombinant DNA which is incorporated into a vector, into an autonomously replicating plasmid or virus, or into the genomic DNA of a prokaryote or eukaryote, or which exists as a separate molecule (i.e., as a cDNA or a genomic or cDNA fragment produced by PCR or restriction enzyme digestion) independent of other sequences. It also includes a recombinant DNA which is part of a hybrid gene encoding additional polypeptide sequence.

In the context of the present invention, the following abbreviations for the commonly occurring nucleic acid bases are used. "A" refers to adenosine, "C" refers to cytosine, "G" refers to guanosine, "T" refers to thymidine, and "U" refers to uridine.

The phrase "under transcriptional control" or "operatively linked" as used herein means that the promoter is in the correct location and orientation in relation to the polynucleotides to control RNA polymerase, initiation and expression of the polynucleotides.

As used herein, the term "promoter/regulatory sequence" means a nucleic acid sequence which is required for expression of as gene product operably linked to the promoter/regulatory sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner.

A "constitutive" promoter is a nucleotide sequence which, when operably linked with a polynucleotide which encodes or specifies a gene product, causes the gene product to be produced in a cell under most or all physiological conditions of the cell.

An "inducible" promoter is a nucleotide sequence which, when operably linked with a polynucleotide which encodes or specifics a gene product, causes the gene product to be produced in a cell substantially only when an inducer which corresponds to the promoter is present in the cell.

A "tissue-specific" promoter is a nucleotide: sequence which, when operably linked with a polynucleotide which encodes or specifies a gene product, causes the gene product to be produced in a cell substantially only if the cell is a cell of the tissue type corresponding to the promoter.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, adenoviral vectors, adeno-associated virus vectors, retroviral vectors, and the like.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (i.e., naked or contained in liposomes) and viruses that incorporate the recombinant polynucleotide.

DESCRIPTION OF THE INVENTION

The present invention provides a hybrid graft and methods of making the hybrid graft. The hybrid method comprises generating a micropatterned surface and a compliant vascular graft whereby the mechanical/elastic properties of the graft can be manipulated by creating aligned nanofibers. Preferably, the hybrid method comprises first generating a micropattern luminal surface by spraying and/or casting a suitable elastomeric polymer onto a micropatterned mandrel, followed by electrospinning a mesh of microfibers on the exterior of the spun casted lumen.

In one aspect, the micropatterned luminal surface is generated by spraying a suitable elastomeric polymer (e.g., polyurethane in a first solution) onto a micropatterned mandrel, followed by electrospinning of the same or another material (in a second solution), which provides the necessary compliance of the entire graft. Accordingly, the hybrid method can be performed on the same electroprocessing device therefore allowing for scale up mass production without the lost of accuracy in the production of the hybrid grafts since this method allows for the mere switching of syringes and solutions on the same setting thereby generating an automatic, controlled method.

Preferably, the spin casting technique is performed on a slowly rotating mandrel, which enables a uniformed transfer of micro-scale features from a 2-D polymer mold to a 3-D structure. The micropatterned grooves produce a directional track on a 3-D graft, which can promote endothelial cell migration from the native tissue into the grafts and improve cell attachment in the graft.

The combination of both electrospinning and spin casting techniques allows for a novel fabrication of artificial grafts with different micro-scale structures to deliver specific cues and functions from the same polymeric material. Preferably, the polymeric material is cholesterol modified polyurethane.

In the present invention, it is demonstrated that the hybrid grafts can be seeded with endothelial cells and the resultant composition can be used for tissue vascularization in viva. In some instances, the implanted hybrid graft can also support additional cell growth in viva, thus providing the ability for tissue reconstruction.

The present invention provides a small diameter vascular graft (e.g., <5 mm) produced by a hybrid method that combines a method of generating a micropatterned luminal surface using electrospraying or casting, and a method of generating an outer envelope that is biocompatible and provides desirable mechanical properties using electrospinning. One advantage of the invention over the art is that the graft of the invention is resistant to oxidation, has limited thrombogenicity, and exhibits enhanced cell attachment, partly because of the use of cholesterol modified polyurethane. Preferably, the luminal surface contains alternating "rings" of cholesterol and an extracellular matrix protein such as fibronectin.

Micropattern

The hybrid grafts of the invention comprises a uniform and well-defined surface topography in the micron scale (microchannel). The hybrid grafts comprise microchannels on the lumen and a mesh of microfibers on the exterior. Preferably, the hybrid graft comprising uniform microchannel and microfiber textures with a size scale less than or equal to about 5 μm.

A micropattern is imposed on the surface of the graft, and comprises a plurality of parallel, elongated grooves separated by plateau regions. The grooves are positioned such that when the device is implanted into a recipient, the grooves are aligned to conform to the desired direction of cell alignment, preferably endothelial cell alignment. The length of the grooves is determined by the intended use of the graft. The width of the grooves is 1 to 30 μm, including any partial or whole increments in between, and is preferably 1-20 μm, more preferably 1-15 μm, more preferably 1-10 μm wide, and most preferably 5 μm wide. The depth of the grooves is 1 to 10 μm, including any partial or whole increments in between, and is preferably 1 to 5 μm, more preferably 1 to 3 μm, and most preferably 1 μm. The grooves are preferably spaced about 1 to 30 μm apart, including any partial or whole increments in between, and is preferably 1-20 μm, preferably 1-15 μm, more preferably 1-10 μm, and most preferably 5 μm. In a preferred embodiment, the grooves have a depth of 1 μm, and a width of 5 μm, and are spaced by plateau regions about equal to the groove width (5 μm). The graft can have a wide variety of groove cross-sectional geometries within these dimensions, including square and rectangular, semi-circular and semi-oval, and v-shaped cross-sections.

In one aspect, the micropattern features can be randomly disposed at the luminal surface. In a further aspect, the micropattern features can be disposed in an ordered arrangement at the luminal surface, in a further aspect, the arrangement of the micropattern features can be predetermined. In an even thither aspect, the micropattern features can be patterned. That is, the micropattern features can be provided by transfer from a mandrel. For example, the micropattern features can be provided by physical transfer from the complementary features of a mandrel. By complementary, it is meant that the micropattern features of the luminal surface are a negative relief of the micropattern features of the mandrel. In this aspect, a pattern can have micropattern features, and the graft is prepared in contact with the mandrel. During preparation, the luminal surface of the graft is provided having micropattern features as a negative relief of the micropattern features of the mandrel. In one aspect, the rotating mandrel used to collect electrospun polymer fibers during preparation of the graft if the invention can function as a pattern. In this aspect, before preparation of the graft, the mandrel is adapted to include complementary micropattern features.

In one aspect, the micropattern features are reservoirs. By "reservoirs," it is meant that the micropattern features comprise a surface having substantially irregular-shaped voids therein. The reservoirs can have an average width of from about 1 μm to about 50 μm, including any partial or whole increments in between, for example, from about 1 μm to about 10 μm, from about 1 μm to about 20 μm, from about 1 μm to about 30 μm, from about 1 μm to about 40 μm. The reservoirs can have an average depth of from about 1 μm to about 10 μm, including any partial or whole increments in between, for example, from about 1 μm to about 9 μm, from about 1 μm to about 8 μm, from about 1 μm to about 7 μm, from about 1 μm to about 6 μm, from about 1 μm to about 5 μm, from about 1 μm to about 4 μm, from about 1 μm to about 3 μm, from about 1 μm to about 2 μm.

In a further aspect, more than one reservoir can be disposed at the luminal surface. In a further aspect, a multiplicity of reservoirs is disposed at the luminal surface.

In a further aspect, the micropattern features can be protrusions or wells. It is understood that both protrusions and wells can be present at the him mat surface. In one aspect, the protrusions comprise raised portions extending outward from the luminal surface. In a further aspect, the protrusions can be substantially round or substantially square masses extending outward from the luminal surface. The protrusions can have an average width of front about 1 μm to about 50 μm, including any partial or whole increments in between, for example, from about 1 μm to about 10 μm, from about 1 μm to about 20 μm, from about 1 μm to about 30 μm, from about 1 μm to about 40 μm. The protrusions can have an average height of from about 1 μm to about 10 μm, including any partial or whole increments in between, for example, from about 2 μm to about 6 μm, from about 2 μm to about 8 μm, from about 3 μm to about 7 μm, from about 4 μm to about 6 μm, or about 5 μm.

In this aspect, wells comprise substantially round or substantially square voids extending inward from the luminal surface. The wells can have an average width of from about 1 pm to about 50 μm, including any partial or whole increments in between, for example, from about 1 μm to about 10 μm, from about 1 μm to about 20 μm, from about 1 μm to about 30 μm, from about 1 μm to about 40 μm, from about 5 μm to about 10 μm, from about 5 μm to about 50 μm, from about 10 μm to about 20 μm, or from about 20 μm to about 30 μm. The wells can have an average depth of from about 1 μm to about 10 μm, including any partial or whole increments in between, for example, from about 2 μm to about 6 μm, from about 2 μm to about 8 μm, from about 3 μm to about 7 μm, from about 4 μm to about 6 μm, or about 5 μm. In a further aspect, more than one protrusion or well can be disposed at the luminal surface. In a further aspect, a multiplicity of protrusions and/or wells is disposed at the luminal surface.

In one aspect, the micropattern features comprise grooves. In this aspect, a groove comprises a canal or ditch extending inward from the interior surface. In one aspect, a groove can be disposed substantially parallel to the direction of the lumen. In this aspect, the groove extends along at least a portion of the length of the lumen. In a further aspect, a groove can be disposed substantially perpendicular to the direction of the lumen. In this aspect, the groove extends along at least a portion of the circumference of the lumen. The grooves can have an average width of from about 1 μm to about 50 μm, including any partial or whole increments in between, for example, from about 1 μm to about 10 μm, from about 1 μm to about 20 μm, from about 1 μm to about 30 μm, from about 1 μm to about 40 μm, from about 5 μm to about 10 μm, from about 5 μm to about 50 μm, from about 10 μm to about 20 μm, or from about 20 μm to about 30 μm. The grooves can have an average height of from about 1 μm to about 10 μm, including any partial or whole increments in between, for example, from about 2 μm to about 6 μm, from about 2 μm to about 8 μm, from about 3 μm to about 7 μm, from about 4 μm to about 6 μm, or about 5 μm. In a further aspect, more than one groove can be disposed at the luminal surface. In a further aspect, a multiplicity of grooves is disposed at the luminal surface.

It is also understood that a combination of reservoirs, protrusions, wells, and/or grooves can be disposed at the interior surface.

In one aspect, the micropattern features comprise grooves disposed on the luminal surface of the graft substantially parallel to the direction of the lumen, in this aspect, the arrangement of the micropattern features can be ordered and predetermined. In a further aspect, the ordered and predetermined micropattern features are patterned. In a further aspect, the substantially parallel grooves extend along al least a portion of the length of the lumen.

Methods for imposing or microfabricating a micropattern on the surface of a graft material can be accomplished using photolithography, microcontact priming, and soft lithography. In a non-limiting example, a silicon mold can microfabricated by coating a silicon wafer with a negative photoresist and exposing it to UV light through a photomask having the desired groove width and length. The photoresist without UV polymerization is developed away, leaving a patterned surface. Then, the silicon wafer is etched by using an ion etcher to form the grooves and the remaining photoresist is washed away. A polymer solution is poured into the silicon mold and allowed to evaporate forming a polymer film.

The graft may be fabricated so as to have differing surface chemistries at the grooves and the plateau regions. For example, the grooves may be optionally coated with a composition to further promote endothelial cell adhesion and differentiation (e.g. extracellular matrix components such as fibronectin, collagen and proteoglycans), and/or the plateau may be coated with a molecule or composition to resist cell adhesion, such as Poly(oligoethyleneglycol methacrylate) (poly-OEGMA) or poly(oligoethyleneglycol methacrylate-co-methacrylic acid) (poly(OEGMA-co-MA)). In particular embodiments, the graft can be constructed and used without any cell adhesion resistant material between the grooves. For simplicity and ease of fabrication, in a preferred embodiment the groove and plateau regions of the device have the same surface chemistry absent any cell adhesion or cell adhesion resistant material.

Surface topography, both microchannels and microfibers, on the lumen of the hybrid gratis provide a physical track to direct the alignment of endothelial cell shape parallel to the directions of channels and fibers. The micro-scale surface topography directs endothelial cell alignment without altering the cells' phenotype. This alignment of endothelial cells emulates the naturally elongated endothelium directed by hemodynamic flow in linear arteries.

The micropatterned grooves induces the alignment of many cell types. For example, when endothelial cells are seeded on the micropatterned surface, the monolayer of endothelial cells emulates the naturally aligned and elongated endothelium in linear vascular vessels under hemodynamic flow environment and guides directional cell migration. The micropatterned grooves demonstrate that the hybrid grafts of the invention allows for endothelialization and provides for a method to recapitulate natural endothelium and potentially facilitate the in vivo healing process after implantation.

The invention relates to a method of preparing a hybrid graft comprising the step of generating a micropatterned luminal surface using a casting and/or spraying technique wherein a suitable elastomeric polymer is casted/sprayed onto a micropatterned mandrel. In one aspect, the method comprises casting/spraying a suitable elastomeric polymer, for example polyurethane, onto a rotating mandrel bearing micropattern features, thereby providing a substantially tubular body having the desired micropatterned grooves.

The instant invention provides a novel hybrid graft fabricated according to the hybrid method of the invention, wherein the modified polyurethane includes those disclosed in U.S. Pat. No. 7,408,014, incorporated herein in its entirety. Preferably, cholesterol modified polyurethane is used in the hybrid method of the invention.

To fabricate hybrid grafts of the invention, microchannels are first produced by spray/spin casting technique disclosed elsewhere herein to the lumen of the graft and then immediately followed by electrospinning to produce microfibers on the outer surface of the graft. One advantage of the present hybrid graft is that a hybrid method comprising spraying/casting a suitable elastomeric polymer to produce a micropatterned luminal surface can further be manipulated by electrospinning the same suitable elastomeric polymer to produce microfibers providing elasticity and necessary compliance of the entire graft.

In one aspect, following spraying/casting a micropatterned luminal surface, the method further comprises the step of electrospinning a polymer onto the sprayed/casted surface thereby providing a substantially tubular body comprising substantially circumferential polymer fibers, wherein the body has an exterior surface and a lumen surface, and wherein the body has complementary micropattern features disposed on the lumen surface.

Electrospinning

Electrospinning as used herein refers to a process in which fibers are formed from a solution or melt by streaming an electrically charged solution or melt through an orifice.

Electrospinning is an atomization process or a fluid which exploits the interactions between an electrostatic field and the fluid. That is, electrospinning is a method of electrostatic extrusion used to produce sub-micron sized fibers. In one aspect, the fluid can be a conducting fluid. Also known within the fiber forming industry as electrostatic spinning, the process of electrospinning generally involves the creation of an electrical field at the surface of a liquid. When an external electrostatic field is applied to a conducting fluid (e.g., a semi-dilute polymer solution or a polymer melt), a suspended conical droplet is formed, whereby the surface tension of the droplet is in equilibrium with the electric field. Electrostatic atomization occurs when the electrostatic field is strong enough to overcome the surface tension of the liquid. The resulting electrical forces create a jet of liquid which carries electrical charge. Thus, the liquid jets may be attracted to other electrically charged objects at a suitable electrical potential. As the jet of liquid elongates and travels, it will harden and dry. Fibrils of nanometer-range diameter can be produced. The hardening and drying of the elongated jet of liquid may be caused by cooling of the liquid, by evaporation of a solvent, or by a curing mechanism. The produced fibers are collected on a suitably located, oppositely charged receiver and subsequently removed from it as needed, or directly applied to an oppositely charged generalized target area.

Fibers can be electrospun from high viscosity polymer melts or polymers dissolved in volatile solvents; the end result is a non-woven mesh of fiber. Solution viscosity can be controlled by modifying polymer concentration, molecular weight, and solvents. Electric field properties can be controlled by modifying bias magnitude or tip-to-target distance. Polymers can be co-spun from same the solution and the polymer phase can be selectively removed. Further, fibers can be electrospun from a multiphasic polymer solution or from an emulsion. For example, polyurethane fibers can be electrospun from a multiphasic polyurethane solution. Emulsifying the solution can increase the solution viscosity, thereby inducing fiber formation at lower concentrations. The resultant fibers can be created having diameters as a function of aqueous content.

Electrospinning is an attractive process for fabricating scaffolds for tissue engineering applications due to the simplicity of the process and the ability to generate microscale and nanoscale features with synthetic and natural polymers. To date, a broad range of polymers has been processed by electrospinning, including polyamides, polylactides, cellulose derivatives, water soluble polymers such as polyethyleneoxide, as well as polymer blends or polymers containing solid nanoparticles or functional small molecules. To date, electrospun fibrous scaffolds have been fabricated with numerous synthetic biodegradable polymers, such as poly($\epsilon$-caprolactone) polylactic acid) (PLA), poly(glycolic acid) (PGA), and the copolymers poly(lactide-co-glycolide) (PLGA). Electrospun scaffolds have been proposed for use in the engineering of bone tissue and cardiac grafts. Similarly, poly(L-lactide-co-$\epsilon$-caprolactone) [P(LLA-CL)] has been electrospun into nanofibrous scaffolds for engineering blood vessel substitutes. However, the invention also includes the use of degradable polymers.

The method of making the hybrid gratis of the invention includes electrospinning the micropatterned material. In the most fundamental sense, the electrospinning apparatus for electrospinning material includes a electrodepositing mechanism and a target substrate. The electrodepositing mechanism includes a reservoir or reservoirs to hold the one or more solutions that are to be electrospun or electrodeposited. The reservoir or reservoirs have at least one orifice or nozzle to allow the streaming of the solution from the reservoirs. One or a plurality of nozzles may be configured in an electrospinning apparatus. If there are multiple nozzles, each nozzle is attached to one or more reservoirs containing the same or different solutions. Similarly, there can be a single nozzle that is connected to multiple reservoirs containing the same or different solutions. Multiple nozzles may be connected to a single reservoir. Because different embodiments involve single or multiple nozzles and/or reservoirs, any references herein to one or nozzles or reservoirs should be considered as referring to embodiments involving single nozzles, reservoirs, and related equipment as well as embodiments involving plural nozzles, reservoirs, and related equipment. The size of the nozzles can be varied to provide for increased or decreased flow of solutions out of the nozzles. One or more pumps used in connection with the reservoirs can be used to control the flow of solution streaming from the reservoir through the nozzle or nozzles. The pump can be programmed to increase or decrease the flow at different points during electrospinning.

The electrospinning occurs due to the presence of a charge in either the orifices or the target, while the other is grounded. In some embodiments, the nozzle or orifice is charged and the target is shown to be grounded. Those of skill in the electrospinning arts will recognize that the nozzle and solution can be grounded and the target can be electrically charged. The creation of the electrical field and the effect of the electrical field on the electroprocessed materials or substances that will form the electroprocessed composition.

Any solvent can be used that allows delivery of the material or substance to the orifice, tip of a syringe, or other site from which the material will be electroprocessed. The solvent may be used for dissolving or suspending the material or the substance to be electroprocessed. Solvents useful for dissolving or suspending a material or a substance depend on the material or substance. Electrospinning techniques often require more specific solvent conditions. For example, polyurethane can be electrospun as a solution or suspension in water, 2,2,2-trifluoroethanol, 1,1,1,3,3,3-hexafluoro-2-propanol (also known as hexafluoroisopropanol or HFIP), or combinations thereof. Alternatively, polyurethane can be electrospun from solvents such as urea, monochloroacetic acid, water, 2,2,2-trifluoroethanol, HFIP, or combinations thereof. Other lower order alcohols, especially halogenated alcohols, may be used. Additional solvents that may be used or combined with other solvents include acetaimide, N-methylformamide, N,N-dimethylformamide (DMF), dimethylsulfaxide (DMSO), dimethylacetamide, N-methyl pyrrolidone (NMP), acetic acid, trifluoroacetic acid, ethyl acetate, acetonitrile, trifluoroacetic anhydride, 1,1,1-trifluoroacetone, maleic acid, hexafluoroacetone. Preferably, cholesterol modified polyurethane is dissolved or suspended in tetrahydrofuran (THF).

In general, when producing fibers using electrospinning techniques, it is preferable to use the monomer of the polymer fiber to be formed. In some embodiments it is desirable to use monomers to produce finer filaments. In other embodiments, it is desirable to include partial fibers to add material strength to the matrix and to provide additional sites for incorporating substances. Preferably, cholesterol modified polyurethane is electrospun to provide mechanical/elastic properties to the hybrid graft of the invention.

In addition to the multiple equipment variations and modifications that can be made to obtain desired results, similarly the electrospun solution can be varied to obtain different results. For instance, any solvent or liquid in which the material is dissolved, suspended, or otherwise combined without deleterious effect on the process or the safe use of the matrix can be used. Materials or the compounds that form materials can be mixed with other molecules, monomers or polymers to obtained the desired results. In some embodiments, polymers are added to modify the viscosity of the solution. In still a further variation, when multiple reservoirs are used, the ingredients in those reservoirs are electrosprayed separately or joined at the nozzle so that the ingredients in the various reservoirs can react with each other simultaneously with the streaming of the solution into the electric field. Also, when multiple reservoirs are used, the different ingredients in different reservoirs can be phased in temporally during the processing period. These ingredients may include other substances.

Embodiments involving alterations to the electrospun materials themselves are within the scope of the present invention. Some materials can be directly altered, for example, by altering their carbohydrate profile. Also, other materials can be attached to the matrix materials before, during or after electrospinning using known techniques such as chemical cross-linking or through specific binding interactions (e.g., PDGF binds to collagen at a specific binding site). Further, the temperature and other physical properties of the process can be modified to obtain different results. The matrix may be compressed or stretched to produce novel material properties.

Electrospinning using multiple jets of different polymer solutions and/or the same solutions with different types and amounts of substances (e.g., growth factors) can be used to prepare libraries of biomaterials for rapid screening. Such libraries are desired by those in the pharmaceutical, advanced materials and catalyst industries using combinatorial synthesis techniques for the rapid preparation of large numbers (e.g., libraries) of compounds that can be screened. For example, the minimum amount of growth factor to be released and the optimal release rate from a fibrous polymer scaffold to promote the differentiation of a certain type of cell can be investigated using the compositions and methods of the present invention. Other variables include fiber diameter and fiber composition. Electrospinning permits access to an array of samples on which cells can be cultured in parallel and studied to determine selected compositions which serve as promising cell growth substrates.

One of ordinary skill in the art recognizes that changes in the concentration of materials or substances in the solutions requires modification of the specific voltages to obtain the formation and streaming of droplets from the tip of a pipette.

The electrospinning process can be manipulated to meet the specific requirements for any given application of the electrospun compositions made with these methods. In one embodiment, the micropipettes can be mounted on a frame that moves in the x, y and z planes with respect to the grounded substrate. The micropipettes can be mounted around a grounded substrate, for instance a tubular mandrel. In this way, the materials or molecules that form materials streamed from the micropipettes can be specifically aimed or patterned. Although the micropipettes can be moved manually, the frame onto which the micropipettes are mounted is preferably controlled by a microprocessor and a motor that allow the pattern of streaming collagen to be predetermined by a person making a specific matrix. Such microprocessors and motors are known to one of ordinary skill in the art. For instance, matrix fibers or droplets can be oriented in a specific direction, they can be layered, or they can be programmed to be completely random and not oriented.

In the electrospinning process, the stream or streams can branch out to form fibers. The degree of branching can be varied by many factors including, but not limited to, voltage, ground geometry, distance from micropipette tip to the substrate, diameter of micropipette tip, and concentration of materials or compounds that will form the electrospun materials. As noted, not all reaction conditions and polymers may produce a true multifilament, under some conditions a single continuous filament is produced. Materials and various combinations can also be delivered to the electric field of the system by injecting, the materials into the field from a device that will cause them to aerosol. This process can be varied by many factors including, but not limited to, voltage (for example ranging from about 0 to 30,000 volts), distance from micropipette tip to the substrate (for example from 0-40 cm), the relative position of the micropipette tip and target (i.e. above, below, aside etc.), and the diameter of micropipette tip (approximately 0-2 mm).

Polymers

In one aspect, the hybrid graft comprises substantially circumferential polymer fibers. In a further aspect, the graft comprises substantially circumferential electrospun polymer fibers.

In one aspect, the polymer fibers can comprise any biocompatible polymer known to those of skill in the art. In a further aspect, the polymer fibers comprise poly(lactic acid), poly(glycolic acid), or poly(ε-caprolactone), or a copolymer thereof, or a mixture thereof. In a further aspect, the polymer of the fibers can be polyethylene and/or polyurethane. In a further aspect, a polymer can be poly(lactide-co-glycolide), polylactic acid), poly(glycolic acid), poly(glaxanone), poly (orthoesters), poly(pyrolic acid), and poly(phosphazenes). Additional polymers that can be used include, but are not limited to, polyalkylene polymers and copolymers, fluorocarbon polymers and copolymers, polyester polymers and copolymers, polyether polymers and copolymers, silicone polymers and copolymers, and polyurethane polymers and copolymers. Other polymers that can be used include, but are not limited to, polyethylenes, polypropylenes, polytetrafluoroethylenes, poly(tetrafluoroethylene-co-hexafluoropropenes), modified ethylene-tetrafluoroethylene copolymers, ethylene chlorotrifluoroethylene copolymers, polyvinylidene fluorides, polyethylene oxides, polyethylene terephthalates, silicones, polyurethanes, polyether block amides, and polyether esters. In a further aspect, the polymer can be one or more polymers, for example, polypyrrole, polyaniline, polythiophene, poly(p-phenylene vinylene), polyparalene, or a mixture thereof. In a further aspect, the polymer can be poly (ethylene-vinyl acetate).

In one aspect, the invention combines the engineering of polymeric fibers with micro-scale patterning of surfaces to design and fabricate superior synthetic conduits, for example vascular grafts derived of biocompatible polymers, for example biomedical grade polyurethane (PU) that offer enhanced biomaterial-cell interaction and functional outcomes, using a spinning, for example electrospinning, construction methodology.

In one aspect, the polymer fibers comprise polyurethane fibers. Such polyurethanes include aliphatic as well as aromatic polyurethanes. In one aspect, useful polyurethanes include aromatic polyether polyurethanes, aliphatic, polyether polyurethanes, aromatic polyester polyurethanes, aliphatic polyester polyurethanes, aromatic polycaprolactam polyurethanes, and aliphatic polycaprolactam polyurethanes. In a further aspect, useful polyurethanes include aromatic polyether polyurethanes, aliphatic polyether polyurethanes, aromatic polyester polyurethanes, and aliphatic polyester polyurethanes.

In a further aspect, the polymer fibers comprise segmented polyurethane fibers, for example, a poly(ether-urethane), a poly(ester-urethane), a poly(urea-urethane), poly(carbonate-urethane), or mixture thereof. In a further aspect, the polymer fibers can be one or more degradable polyurethanes derived from glycerol and sebacic acid. See Wang Y., Ameer G. A., Sheppard Langer R., A tough biodegradable elastomer, Nature Biotechnology, 2002, 20(6)602-606. In a further aspect, the polymer fibers comprise medical grade and/or FDA-approved polyurethane fibers.

The chemistry of polyurethanes is extensive and well developed. Typically, polyurethanes are made by a process in which a polyisocyanate is reacted with a molecule having at least two hydrogen atoms reactive with the polyisocyanate, such as a polyol. That is, the polyurethane can be the reaction product of the following components: (A) a polyisocyanate having at least two isocyanate (—NCO) functionalities per molecule with (B) at least one isocyanate reactive group, such as a polyol having at least two hydroxy groups or an amine. Suitable polyisocyanates include diisocyanate monomers, and oligomers. The resulting polymer can be further reacted with a chain extender, such as a diol or diamine, for example. The polyol or polyamine can be a polyester, polyether, or polycarbonate polyol, or polyamine, for example.

Polyurethanes can be tailored to produce a range of products from soft and flexible to hard and rigid. They can be extruded, injection molded, compression molded, and solution spun, for example. Thus, polyurethanes can be important biomedical polymers, and are used in implantable devices such as artificial hearts, cardiovascular catheters, pacemaker lead insulation, etc.

In one aspect, the polymer fibers comprise a commercially available polyurethane useable for implantable applications. Commercially available polyurethanes used for implantable applications include ST1882 segmented polyether aromatic polyurethanes available from Stevens Urethane, Easthampton, Mass.; BIOSPAN™ segmented polyurethanes available from Polymer Technology Group of Berkeley, Calif.; PELLETHANE™ segmented polyurethanes available from Dow Chemical, Midland, Mich.; and TECOFLEX™ and TECOTHANE™ segmented polyurethanes available from Thermedics, Inc., Woburn, Mass. These polyurethanes and others are described in the article "Biomedical Uses of Polyurethanes," by Coury et al., in Advances in Urethane Science and Technology, 9, 130-168, eds. K. C. Frisch and D. Klempner, Technomic Publishing Co., Lancaster, Pa., (1984). Typically, polyether polyurethanes exhibit more biostability than polyester polyurethanes, and are therefore generally preferred polymers for use in biological applications.

Polyether polyurethane elastomers, such as PELLETHANE™ 2363-80A (P80A) and 2363-55D (P55D), which can be prepared from polytetramethylene ether glycol (PTMEG) and methylene bis(phenylisocyanate) (MDI) extended with butanediol (BDO), are widely used for implantable cardiac pacing leads. Pacing lends are insulated wires with electrodes that carry stimuli to tissues and biologic signals back to implanted pulse generators. The use of polyether polyurethane elastomers as insulation on such leads has provided significant advantage over silicone rubber, primarily because of the higher tensile strength and elastic, modulus of the polyurethanes.

Examples of commercial polyurethanes that can be used in connection with the invention include TECOFLEX™, TECOTHANE™, and BIOSPAN™ polyurethanes. TECOFLEX™ segmented polyurethanes are a family of aliphatic, polyether-based thermoplastic polyurethanes (TPUs) available over a wide range of diameters, colors, and radiopacifiers. These resins are generally easy to process and typically do not yellow upon aging, TECOTHANE™ segmented polyurethanes are a family of aromatic, polyether-based TPUs available over a wide range of durometers, colors, and radiopacifiers. Generally, TECOTHANE™ resins exhibit improved solvent resistance and biostability when compared with TECOFLEX™ resins of equal durometer. As with any aromatic polyurethane, TECOTHANE™ resins can tend to yellow upon aging or when subjected to radiation sterilization. BIOSPAN™ segmented polyurethane (SPU) is a biomaterial widely used in clinical ventricular assist devices and artificial heart cases. It is one of the most extensively tested biomaterials on the market. BIOSPAN™ is an elastomeric biomaterial exhibiting a superior combination of physical and mechanical properties together with biological compatibility.

Further examples of commercial polyurethanes that can be used in connection with the invention include Sancure 2710™ and/or Avalure UR 445™ (which are equivalent copolymers of polypropylene glycol, isophorone diisocyanate, 2,2-dimethylolpropionic acid, having the International Nomenclature Cosmetic Ingredient name "PPG-17/PPG-34/IPDI/DMPA Copolymer"), Sancure 878™, Sancure 815™, Sancure 1301™, Sancure 2715™, Sancure 1828™, Sancure 2026™, Sancure 1818™, Sancure 853™, Sancure 830™, Sancure 825™, Sancure 776™, Sancure 850™, Sancure 12140™, Sancure 12619™, Sancure 835™, Sancure 843™, Sancure 898™, Sancure 899™, Sancure 1511™, Sancure 1514™, Sancure 1517™, Sancure 1591™, Sancure 2255™, Sancure 2260™, Sancure 2310™, Sancure 2725™, and Sancure 12471™ (all of which are commercially available from BFGoodrich, Cleveland, Ohio), Bayhydrol DLN (commercially available from Bayer Corp., McMurray, Pa.), Bayhydrol LS-2033 (Bayer Corp.), Bayhydrol 123 (Bayer Corp.), Bayhydrol PU402A (Bayer Corp.), Bayhydrol 110 (Bayer Corp.), Witcobond W-320 (commercially available from Witco Performance Chemicals), Witcobond W-242 (Witco Performance Chemicals), Witcobond W-160 (When Performance Chemicals), Witcobond W-612 (Witco Performance Chemicals), Witcobond W-506 (Witco Performance Chemicals), NeoRez R-600 (a polytetramethylene ether urethane extended with isophorone diamine commercially available from Avecia, formerly Avecia Resins), NeoRez R-940 (Avecia Resins), NeoRez R-960 (Avecia Resins), NeoRez R-962 (Avecia Resins), NeoRez R-966 (Avecia Resins), NeoRez R-967 (Avecia Resins), NeoRez R-972 (Avecia Resins), NeoRez R-9409 (Avecia Resins), NeoRez R-9637 (Avecia), NeoRez R-9649 (Avecia Resins), and NeoRez R-9679 (Avecia Resins).

In a further aspect, the polymer fibers are aliphatic polyether polyurethanes. Examples of such aliphatic polyether polyurethanes include Sancure 2710™ and/or Avalure UR 445™, Sancure 878™, NeoRez R-600, NeoRez R-966, NeoRez R-967, and Witcobond W-320.

In one aspect, the hybrid graft can further comprise a supplementary material. The supplementary material can be any supplementary material known to those of skill in the art and can be selected to modify the properties of the polymer fibers. For example, cellular adhesion can be improved by incorporation of soluble type I collagen into the scaffold by co-spinning the collagen from a solution of 1,1,1,3,3,3-hexafluoro-2-propanol using a dual needle system. Another supplementary material useful for cellular adhesion is fibronectin. The supplementary material can be added to the spinning solution to produce the polymer fibers. In a further aspect, the supplementary material can be added to the polymer fibers after spinning. In various aspects, the supplementary material comprises polymer fibers, a polymer network, or a coating.

In one aspect, the supplementary material comprises collagen, fibrin, chitin, laminin, polyethylene glycol, or a mixture thereof. In a father aspect, the supplementary material comprises a synthetic peptide, a polysaccharide, a proteoglycan, or an extracellular matrix component.

Application

In one aspect, the hybrid graft of the invention is a conduit. The exterior surface of the hybrid graft comprises a mesh of electrospun fibers. In some instances, the electrospun fibers on the exterior surface provides mechanical/elastic properties to the graft. Preferably, the mechanical property of the hybrid graft is within the same range as the mechanical property of a natural artery.

The hybrid grafts of the invention comprises a luminal surface that supports the attachment and growth of cells. The hybrid grafts of the invention can be seeded with cells prior to implantation of the device. Typically, the cells are autologous endothelial cells.

In this aspect, the vascular graft can comprise a substantially tubular body comprising substantially aligned, substantially circumferential, electrospun polyurethane fibers; wherein the body has an exterior surface and a lumen surface. The graft has as diameter of about 4 mm extending therethrough; wherein the body has microscale grooves disposed at the lumen surface substantially parallel to the length of the conduit; wherein the grooves have an average width of about 5 µm and an average depth of about 1 µm and each groove is spaced about 5 µm apart; wherein at least one endothelial cell is adhered to the lumen surface. The grooves on the luminal surface allows for endothelial cells to attach and grow into or line the luminal surface of the graft. However, the invention is not limited to endothelial cells. Any cell types that can attach to, and grow on the grooves is included in the invention. Any cell type that lines the lumen can be used. For example, epithelial cells of any type can be attached to the luminal surface of the graft. One of skill in the art can determine what type of cell to attach to the luminal surface of the graft. Moreover, different cells can attach to the lumen surface of the graft in vivo depending on where in the body the graft is placed.

The graft of the invention can be used, for example, to replace a length of tubular organs such as vasculature, ureters, urethra, esophagus, trachea, intestine, vas deferens and fallopian tubes. The graft can also be used as a nerve growth guidance channel or other tubular prostheses.

These organs have a basic tubular shape with an outer surface and an inner luminal surface. The graft's inner luminal surface can be lined or coated with cells in vitro or in vivo. For example, if the graft is to be used to replace a section of vasculature, endothelial cells can be cultured and attached onto the luminal surface of the graft in vitro before placement into a subject. Similarly, if a section of urethra or ureter is to be replaced, the appropriate epithelial cell type can be cultured and attached to the graft in vitro prior to insertion into the ureter or urethra. Alternatively, the graft can be inserted into the appropriate region of the body without any cellular attachment. If the graft is inserted without cells, the subject's own cells attach to the graft in vivo. Moreover, a combination of the in vitro and in vivo approach can also be used. For example, a given number of cells can be attached or seeded onto the graft in vitro, and then the graft can be inserted into a subject where additional cells of the subject can attach to the already seeded graft.

Prior to implantation, the surface of the hybrid graft may be seeded with cells using known methods. The cells are allowed to adhere to the grooves and the graft is implanted into a recipient, in certain embodiments, the graft may be seeded with endothelial cells. For example, the graft may be fabricated to form a vessel having a luminal surface that is seeded with endothelial cells, wherein the luminal surface is micropatterned with the grooves aligned circumferentially around the vessel. The endothelialized graft may be implanted into a recipient where endogenous cells adhere to the grooves. Alternatively, the endothelialized graft may also be seeded with cells that adhere to the grooves prior to implantation. In a further embodiment, the graft may be seeded with cells that adhere to the grooves forming a monolayer of cells.

The micropattern grooves on the luminal surface of the graft promotes cell adhesion and cell alignment and enabling the cells to maintain their in vivo functions. Endothelization allows for the use of the hybrid grafts in treating vascular diseases because the graft functions similar to a natural vascular endothelium. The recipient can be any mammal in need of vascular graft therapy. In one embodiment, the recipient is an animal model of restenosis and vascular disease (e.g. moose, rabbit, pig, etc.). In a preferred embodiment the recipient is human.

With respect to a nerve growth guidance channel, the hybrid graft of the invention can be used to treat damaged nerve. Accordingly, the invention is applicable to the peripheral and the central nervous system. In some instances, the hybrid graft is useful for treating spinal cord injury. Where the damaged neural pathway results from CNS axonal damage, autologous peripheral nerve grafts have been used to bridge lesions in the central nervous system and to allow axons to make it back to their normal target area. In contrast to CNS neurons, neurons of the peripheral nervous system can extend new peripheral processes in response to axonal damage. This regenerative property of peripheral nervous system axons is thought to be sufficient to allow grafting of these segments to CNS axons.

Within the peripheral nervous system, the cellular regenerative property of neurons can be promoted using the hybrid graft of the invention thereby repairing or promoting regeneration to a damaged neural pathway.

Genetic Modification

Cell cultures can be established from mammalian, or other, tissue sources by dissociating the tissue or by an explant method. Primary cultures can be established and cryopreserved in master cell banks from which portions of the bank can be thawed, seeded, and subcultured to expand cell numbers. To populate an acellular scaffold with cells, the scaffold can be placed in a culture dish or flask and contacted by immersion in media containing suspended cells.

Although human cells are preferred for use in the invention, the cells to be used are not limited to cells from human sources. Cells from other mammalian species including, but not limited to, equine, canine, porcine, bovine, ovine, and murine sources may be used. Cell donors may vary in development and age. Embryonic progenitor cells such as stem cells may be used in the invention and induced to differentiate to develop into the desired tissue.

The hybrid graft of the invention having a tubular structure can have smooth muscle cells in contact with the exterior surface of the tubular structure. Smooth muscle cells can form a confluent tubular sheet surrounding the tubular structure. The hybrid graft can have endothelial cells in contact with the interior surface of the tubular structure. Endothelial cells can be positioned within linear reservoirs in the interior surface or can form a confluent tubular sheet in contact with the interior surface of the tubular structure.

Cells that can be used in connection with the invention include a chondroblast, a chondrocyte, a fibroblast, a transfected fibroblast, an endothelial cell, an osteoblast, an osteocyte, an epithelial cell, an epidermal cell, a mesenchymal cell, a hemopoietic cell, an embryoid body, a nerve cell, a Schwann cell, a glial cell, a stein cell, dorsal root ganglia, and mixtures thereof.

In addition, genetically engineered cells that are spontaneously, chemically, or virally transfected may also be used in this invention. Recombinant or genetically-engineered cells may be used to create a tissue construct that acts as a drug delivery graft for a subject needing increased levels of natural cells products or treatment with a therapeutic. The cells can produce and deliver to the patient via the graft recombinant cells products, growth factors, hormones, peptides or proteins for a continuous amount of time or as needed when biologically, chemically, or thermally signaled due to the conditions present in the patient.

Genetically modified cells are also useful in the instant invention. Preferably, the cells are endothelial cells. Genetic modification may, for instance, result in the expression of exogenous genes ("transgenes") or in a change of expression of an endogenous gene. Such genetic modification may have therapeutic benefit. Alternatively, the genetic modification may provide a means to track or identify the cells so-modified, for instance, after implantation of a composition of the invention into an individual. Tracking a cell may include tracking migration, assimilation and survival of a transplanted genetically-modified cell. Genetic modification may also include at least a second gene. A second gene may encode, for instance, a selectable antibiotic-resistance gene or another selectable marker.

Proteins useful for tracking a cell include, but are not limited to, green fluorescent protein (OFF), any of the other fluorescent proteins (e.g., enhanced green, cyan, yellow, blue and red fluorescent proteins; Clontech, Palo Alto, Calif.), or other tag proteins (e.g., LacZ, FLAG-tag, Myc, $His_6$, and the like).

When the purpose of genetic modification of the cell is for the production of a biologically active substance, the substance will generally be one that is useful for the treatment of a given disorder. For example, it may be desired to genetically modify cells so that they secrete a certain growth factor product associated with bone or son tissue formation. Growth factor products to induce growth of other, endogenous cell types relevant to tissue repair are also useful. For instance, growth factors to stimulate endogenous capillary and/or microvascular endothelial cells can be useful in repair of soft tissue defect, especially for larger volume defects.

The cells of the present invention can be genetically modified by having exogenous genetic material introduced into the cells, to produce a molecule such as a trophic factor, a growth factor, a cytokine, and the like, which is beneficial to culturing the cells. In addition, by having the cells genetically modified to produce such a molecule, the cell can provide an additional therapeutic effect to the mammal when transplanted into a mammal in need thereof. For example, the genetically modified cell can secrete a molecule that is beneficial to cells neighboring the transplant site in the mammal.

The cells may be genetically modified using any method known to the skilled artisan. See, for instance, Sambrook et al, (2001, Molecular Cloning: A Laboratory Manual, Cold Spring Harbor Laboratory Press, Cold Spring Harbor, N.Y.), and in Ausubel et al. Eds, (1997, Current Protocols in Molecular Biology, John Wiley & Sons, New York, N.Y.). For example, a cell may be exposed to an expression vector comprising a nucleic acid including a transgene, such that the nucleic acid is introduced into the cell under conditions appropriate for the transgene to be expressed within the cell. The transgene generally is an expression cassette, including a polynucleotide operably linked to a suitable promoter. The polynucleotide can encode a protein, or it can encode biologically active RNA (e.g., antisense RNA or a ribozyme). Thus, for example, the polynucleotide can encode a gene conferring resistance to a toxin, a hormone (such as peptide growth hormones, hormone releasing factors, sex hormones, adrenocorticotrophic hormones, cytokines (e.g., interferons, interleukins, lymphokines), etc.), a cell-surface-bound intracellular signaling moiety (e.g., cell adhesion molecules, hormone receptors, etc,), a factor promoting a given lineage of differentiation (e.g., bone morphogenic protein (BMP)), etc.

Within the expression cassette, the coding polynucleotide is operably linked to a suitable promoter. Examples of suitable promoters include prokaryotic promoters and viral promoters (e.g., retroviral ITRs, LTRs, immediate early viral promoters (IEp), such as herpesvirus IEp (e.g., ICP4-IEp and ICP0-TEEp), cytomegalovirus (CMV) IEp, and other viral promoters, such as Rous Sarcoma Virus (RSV) promoters, and Murine Leukemia Virus (MLV) promoters). Other suitable promoters are eukaryotic promoters, such as enhancers (e.g., the rabbit β-globin regulatory elements), constitutively active promoters (e.g., the β-actin promoter, etc.), signal specific promoters (e.g., inducible promoters such as a promoter responsive to RU486, etc.), and tissue-specific promoters. It is well within the skill of the art to select a promoter suitable for driving gene expression in a predefined cellular context. The expression cassette can include more than one coding polynucleotide, and it can include other elements (e.g., polyadenylation sequences, sequences encoding a membrane-insertion signal or a secretion leader, ribosome entry sequences, transcriptional regulatory elements (e.g., enhancers, silencers, etc.), and the like), as desired.

The expression cassette containing the transgene should be incorporated into a genetic vector suitable for delivering the transgene to the cells. Depending on the desired end application, any such vector can be so employed to genetically modify the cells (e.g., plasmids, naked DNA, viruses such as adenovirus, adeno-associated virus, herpesviruses, lentiviruses, papillomaviruses, retroviruses, etc.). Any method of constructing the desired expression cassette within such vectors can be employed, many of which are well known in the art (e.g., direct cloning, homologous recombination, etc.). The choice of vector will largely determine the method used to introduce the vector into the cells (e.g., by protoplast fusion calcium-phosphate precipitation, gene gun, electroporation, DEAE dextran or lipid carrier mediated transfection, infection with viral vectors, etc.), which are generally known in the art.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following, examples, but rather, should be construed to encompass any and all variations which become evident as a result of the teaching provided herein.

Example 1

Micropatterning of Electrospun Tissue-Engineered Vascular Grafts

The lack of endothelialization in small caliber vascular conduits remains the major challenge for the successful healing of artificial grafts to native blood vessels. The following experiments were designed to fabricate three-dimensional (3-D), micropatterned polyurethane grafts that possess mechanical property of natural artery, promote cell alignment and enable the cells to maintain their in vivo functions. As a non-limiting example, grafts with about a diameter of 4 mm were constructed using a hybrid method comprising electrospinning and spin casting techniques to create uniform microfibers and microchannels, respectively, on the lumen. The combination of both techniques resulted in a hybrid graft, which exhibited microchannels on the lumen and mesh of electrospun microfibers on the exterior.

After precoating grafts with fibronectin, bovine aortic and human umbilical vein-derived EA.hy926 endothelial cells were seeded on the grafts inside rotating bioreactors. At confluence, individual cells in the monolayer aligned parallel to microfibers and microchannels as visualized by immunostained VE-cadherin, fluorescently-labeled actin microfilaments and scanning electron microscopy. When the cells were treated with tumor necrosis factor-α, ICAM-1 expression was upregulated and human monocytic U937 cells adhered to the stimulated endothelial monolayer. The results presented herein demonstrate that the 3-D micropatterned polyurethane gratis can recapitulate the in vivo morphology and function of natural vascular endothelium.

The materials and methods employed in these experiments are now described.

Fabrication of Polyurethane Grafts

Tecothane, an aromatic polyether polyurethane, was purchased from Thermedics Inc. (Woburn, Mass.), purified and characterized as previously described (Stachelek et al., 2005 J Biomed Mater Res A 72(2):200-12). The purified polyurethane (PU) was dissolved in 1,1,1,3,3,3-hexafluoro-2-propanol (HFP) (Sigma, St. Louise), yielding 3% and 5% (w/v) solutions for spin casting and electrospinning, respectively. The 5% PU solution used for electrospinning was shown to produce uniform microfibers without any formation of beads along the fiber length. Mandrels with 4-mm diameter were custom made from aluminum rods. PU grafts with three different types of topographies, microchannels, microfibers and combined microchannels and mesh were fabricated as described elsewhere herein.

PU grafts with microchannels oriented along the graft length were fabricated by spin casting method. Microchannels (3.6 μm channel×3.3 μm ridge×1 μm depth) were first fabricated on silicon wafer and then transferred to poly(dimethylsiloxane) (PDMS) (Robert McKeown, Inc., Branchburg, N.J.) as previously described (Uttayarat et al., 2005, J Biomed Mater Res 75(3):668-80). This micropatterned PDMS sheet (2.5×2.5 cm and 200 μm thick) was wrapped around a mandrel and secured with nail polisher to create a 3-dimensional mold with microchanneled surface exposed to air. After drying overnight, about 2 ml of 3% PU solution was cast on the mandrel while slowly rotating under high intensity halogen lamp (300 W) for 30 min to transfer the microchannel patterns from PDMS to PU. The as-cast PU graft of 2.5 cm in length was dry tinder the laminar flow inside the hood overnight before released from the mandrel. Microchannels and graft thickness, determined from the cross-sectional view, were subsequently inspected by SEM.

Using the electrospinning method, PU grafts were constructed from electrospun PU microfibers that helically wrapped around the mandrel. The electrospinning apparatus was setup as previously described (Li et al., 2006, J Biomed Mater Res A, 79(4):963-73). In brief, a power supply, a syringe pump speed, and a distance between the pump and a copper plate were set at 12 kV, 0.8 and 12 cm, respectively. A high speed drill was placed in front of the copper plate to collect jet of PU solution produced across an electric field created between the syringe and copper electrodes. At 35,000 rpm rotation speed, the collected PU microfibers became helically oriented on the rotated mandrel. About 2 ml of 5% PU solution were used to fabricate one electrospun graft of about 5 cm in length. Then the PU grafts were released from mandrel after drying for overnight. The fiber dimension as well as graft thickness were inspected by SEM.

To fabricate hybrid PU grafts with combined microchannel and mesh topographies, microchannels were first produced by spin casting 3% PU solution on PDMS-wrapped mandrel and then immediately followed by electrospinning with 5% PU solution at about 50 rpm. This lower rotation speed provided mesh of PU microfibers on the outer surface of the graft. Both luminal and outer surfaces were then inspected by SEM.

Mechanical Characterization

The elastic moduli of PU grafts were measured using Instron (model 5564 with the Merlin version 9.0 software) under tensile mode. PU grafts were cut into rectangular specimens with thicknesses determined by SEM. For electrospun grafts, each graft was cut circumferentially (parallel to the fiber direction) and longitudinally (orthogonal to the fiber direction) with respect to the graft length. The crosshead speed was set at 5 min in on the 0.1 N load transducer. Each specimen was strained to 50% from its original length for 10 cycles and then to 300% to test whether it could withstand the tensile force or failed. Data were recorded as load and displacement.

Cell Culture

Bovine aortic endothelial cells (BAECs) were isolated and cultured in gelatin-coated T75 flasks using Dulbecco's modified Eagle's medium (DMEM) (Mediatech) supplemented with 10% PBS (Hyclone), 1 mg/ml glucose, 0.3 mg/ml L-glutamine, 10 μg/ml streptomycin, 10 U/ml penicillin, and 25 ng/ml amphotericin (complete DMEM). Cells were sub-cultured every two days and used at passages 5-12. Human umbilical vein-derived EA.hy926 endothelial cells were kindly provided by Professor Edgell at University of North Carolina, Chapel Hill. Cells were kept in culture in gelatin-coated T75 flasks using DMEM supplemented with 10% FBS, 4.5 mg/ml glucose, 100 μg/ml streptomycin and 100 U/ml penicillin. Cells were sub-cultured every two days and passages 30-42 were used in the experiments. Human monocytic U937 cells (American Type Culture Collection) were cultured in RPMI-1640 supplemented 10% FBS, 100 μg/ml streptomycin and 100 U/ml penicillin. Cells were sub-cultured when the cell density reached $10^6$ cells/ml. All BAECs, human umbilical vein-derived. EA.hy926 endothelial cell and human monocytic U937 cells were maintained in 95% air/5% $CO_2$.

Endothelialization of PU Grafts

Before cell seeding, PU grafts were sterilized by immersion in a solution containing streptomycin, penicillin and amphotericin (ABAM) (Mediatech). The as-received ABAM stock was diluted in tissue culture water at 1:10, 1:50 and 1:100 (v/v), PU grafts were immersed in diluted ABAM solutions, each dilution for one day, followed by rinsing in PBS. To promote initial endothelial cell attachment on PU grafts, all spun east and electrospun grafts were incubated in 10 μg/ml fibronectin (Fn) (Sigma) solution overnight and non-specific adhesion was blocked in 1% BSA (Sigma) as previously described (Uttayarat et al., 2005, J Biomed Mater Res 75(3):668-80).

PU grafts were placed inside bioreactors made from 3-ml syringes capped with lure locks and plungers. BAECs and EA.hy926 endothelial cells were harvested at 90% confluence and resuspended in DMEM supplemented with 25 mM HEPES (Mediatech) to maintain physiological pH in the absence of $CO_2$ in closed bioreactors. A 2-ml cell suspension, with cell density of 500,000 cells/ml, was added to each syringe. After air bubbles were vented out of the syringes, the lure locks were tightly closed and all syringes were rotating on an orbital shaker inside the incubator for 2 hours. To provide uniform cell density, each syringe on the orbital shaker was manually turned around its long axis at positions north, south, east and west every five minutes. Followed this initial cell seeding step, each graft was then transferred to a T-25 flasks filled with complete DMEM or fixed in 4% formaldehyde (Fisher) at room temperature for 15 min to visualize initial cell distribution. The medium was refreshed everyday for extended culture time.

Fluorescence Imaging of Endothelial Monolayer

To visualize the formation of endothelial monolayer on the lumen of PU grafts, BAECs and EA.hy926 endothelial cells were immunostained for VE-cadherin, the phenotypic marker for the adhesion molecule expressed in vascular endothelial cells. In addition, actin microfilaments were also visualized by TRITC-conjugated phalloidin using the staining protocol previously described (Uttayarat et al., 2005 J Biom Mat Res 75A: 668). To immunostain for VE-cadherin, goat polyclonal IgG (Santa Cruz Biotechnology, Inc., Santa Cruz, Calif.) and chicken anti-goat IgG (Molecular Probe, Eugene, Oreg.) served as primary and secondary antibodies, respectively. All antibodies were diluted in PBS. After fixation in cold ($-20°$ C.) methanol for 5 min, the samples were rinsed and stained with 1:40 goat polyclonal IgG for 1 h at room temperature. Followed three washes in PBS, 10 min per wash, the samples were incubated in a solution containing 1:1000 chicken anti-goat IgG for 45 min at room temperature. The samples were then washed three times in PBS. 10 min for each wash. A 20-µl drop of Vectashield with DAPI (Vector Lab, Burlingame, Calif.) was then added to each sample before it was mounted on glass slide and covered with cover slip. Fluorescence images were then taken by conventional fluorescence microscope (Leica DMRX).

Scanning Electron Microscopy

The topography of microchannels and microfibers on the lumen of PU grafts as well as the formation of endothelial monolayer was visualized using SEM (FEI XL30, Drexel University). The cross-section (orthogonal to the graft length) and the luminal surface of the graft were mounted on aluminum stubs before sputtered coated with platinum. For grafts seeded with endothelial cells, the samples were fixed after live days in culture in 2% gluteraldehyde at 4° C. for 45 min, rinsed in sodium cacodylate buffer and briefly rinsed in tissue culture-grade water. Using 5-min immersion times, cells were then dehydrated sequentially in water-ethanol solutions containing 5%, 30%, 50%, 75% and 90% ethanol and twice in 100% ethanol. The samples were then critical point dried by CPD 7501 (SPI Supplies, Westchester, Pa.) before being visualized using SEM.

Flow Cytometry and Monocyte Adhesion Assay

The induced ICAM-1 expression of endothelial cells due to activation by pro-inflammatory TNF-α was measured by flow cytometry. Due to the feasibility to harvest cells and to rule out the implication from the pre-coating Fn, EA.hy926 endothelial cells were cultured on cast, non-treated PU films in 24-well tissue culture plates. After one day post confluence, cells were incubated for 16 hours in TNF-α (Sigma) at concentrations 0 (control) and 10 ng/ml. Approximately $5 \times 10^5$ wits from each treatment were harvested in 0.005% Trypsin-EDTA solution (Sigma) and re-suspended twice in cold PBS with 20 mM EDTA and 1% BSA (blocking buffer) at 4° C. for 5 min (Labofuge 400, Thermo Scientific). The cells were then incubated in phycoerythrin anti-mouse CD54 (1:5 dilution, eBioscience) for 30 min on ice, followed by three re-suspensions in blocking buffer. For comparison, cells treated with 10 ng/ml TNF-α were also immunostained for their isotype with anti-rat IgG2b (eBioscience). For all experiments, 50,000 events per sample were collected for analysis on a BD (San Jose, Calif.) FACSCanto flow cyometer using FACSDiva software.

In addition to TNF-α induced ICAM-1 expression, the adhesion of monocytes to activated endothelial cells was also determined. Human monocytic U937 cells were prelabled with 1 µg/ml biz-benzamide (BBZ) (Sigma) in RPMI for 10 min. After 16 hours incubation in 10 ng/ml TNF-α, the DNA-labeled U937 cells were plated on the endothelial monolayer grown on cast PU surfaces at a density of $20 \times 10^3$ cells/ml for 30 min. Following three washes in PBS on the orbital shaker, the monolayer was fixed in 4% formaldehyde and stained with TRITC-conjugated phalloidin. The attached monocytes on endothelial cells were visualized by fluorescence microscope.

Data Analysis

For electrospun, spun cast and hybrid grafts, the dimensions of electrospun fibers, ridges, channels, channel depths and graft thicknesses were determined from about 5-8 SEM images for each sample. To determine the elastic moduli of the fabricated PU grafts, about 3-5 specimens for each of the electrospun, spun cast and hybrid grafts were tested using Instron under tensile mode. To quantify the response of endothelial cells to the pro-inflammatory stimulus TNF-α, ICAM-1 expression was analyzed by FlowJo software (Treestar, Ashland, Oreg. USA) from three independent experiments and the number of adhered monocytes was determined from fluorescence images.

Statistical Analysis

Data are expressed as mean±standard error of mean. Statistical analysis was performed by one-way ANOVA, followed by post-hoc Tukey's t-test with $p \leq 0.05$ being statistically significance.

The results of the experiments are now described.

Morphology of Polyurethane Grafts

Figure 2:
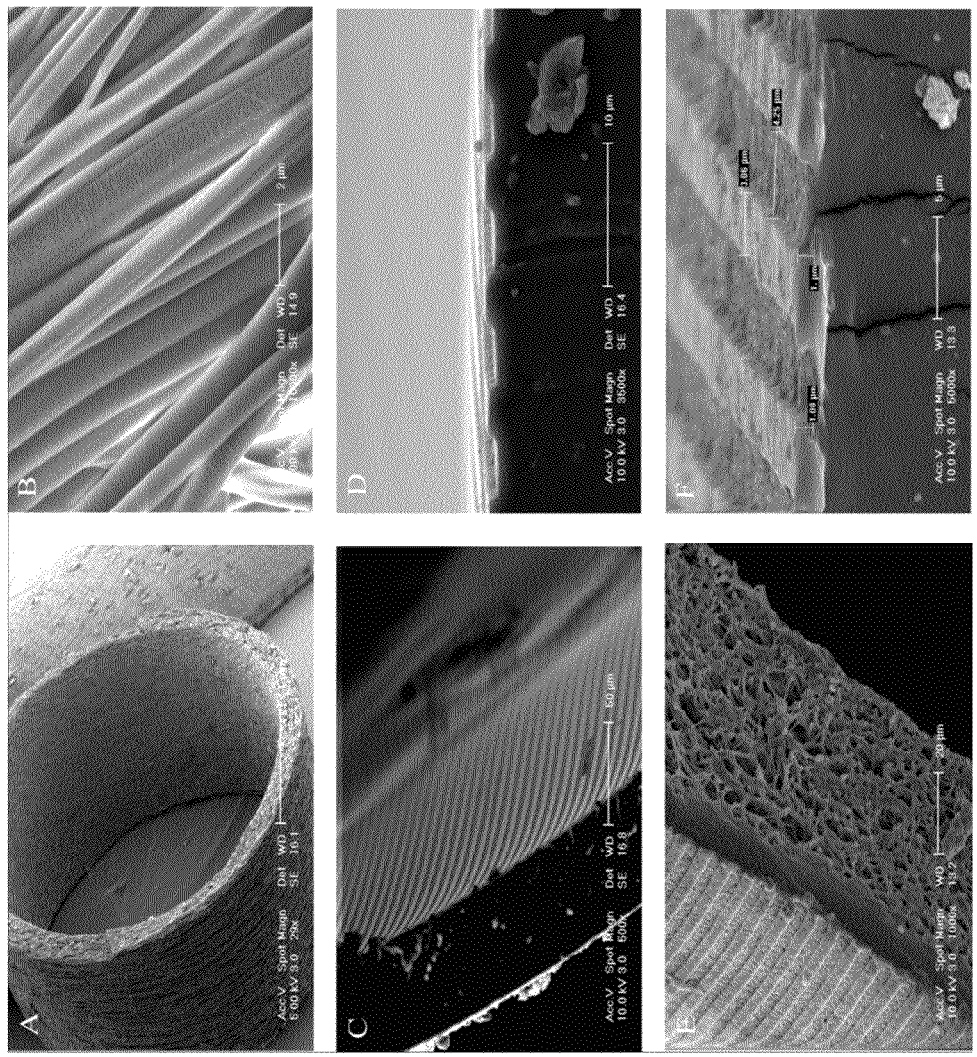
FIG. 2, comprising

Small caliber PU grafts with uniform and well-defined surface topography in the micron scale can be fabricated by a combination of electrospinning and spin casting (FIG. 1). During the electrospinning process, PU fibers were collected on a high speed, rotating mandrel, resulting in the uniform alignment of microfibers helically along the mandrel (FIG. 2A). At 5% (w/v) concentration, individual PU fiber had a smooth surface and the fiber diameter was about 1.2 (±0.3) µm (FIG. 2B). Lower concentration of PU in the solution led to the formation of beads along the fiber length. Inspected by SEM, the total graft thickness was 193.3 (±12.3) µm.

For grafts fabricated by spin casting technique, the pattern of microchannels was successfully transferred from PDMS to PU surface (FIG. 2C). The channel width, ridge width and channel depth were maintained at about 3.9 (±0.1), 3.6 (±0.2) and 0.9 (±0.03) µm, respectively (FIG. 2D), similar to the original dimension of microchannels fabricated on silicon wafer. The thickness of spun cast grafts was about 65.8 (±3.5) µm.

The combined spin casting and electrospinning techniques yielded hybrid PU grafts with microchannels on the lumen and mesh of microfibers on the exterior (FIG. 2E). Unlike the spun cast PU grafts, these hybrid grafts exhibited a rougher microchanneled surface, which is believed to be due to a shorter solvent evaporation time between spin casting and electrospinning steps. Despite this information of micro bumps on the ridges and channels, the channel dimension (FIG. 2F) remained similar to that of the spun cast graft. The thickness of hybrid grafts was about 59.4 (±1.3) µm. The results presented herein demonstrate that a hybrid graft comprising uniformed microchannel and microfibered textures that has a size scale ≤5 µm can be fabricated on the lumens of small caliber artificial grafts using spin casting and electrospinning techniques.

Mechanical Properties of Polyurethane Grafts

The elastic moduli of electrospun and spun cast polyurethane grafts were determined from the slope of stress-strain plot obtained from the Instron test and tabulated in Table 1.

For electrospun grafts, the elastic modulus varied with the orientation of microfibers that constituted the grafts. Measured parallel to the fiber direction (transverse to the graft length), the elastic modulus was 3.43 (±0.98) MPa, about eight times higher than the modulus of 0.43 (±0.04) MPa measured in the direction perpendicular to microfibers (along the graft length). As a comparison, the modulus of electrospun PU sheet containing isotropic mesh of microfibers was 1.25 (±0.28) MPa, which lied between the values determined from grafts with oriented microfibers. Without any fibrous constituents, the elastic modulus of spun cast grafts was slightly higher than electrospun grafts measured transverse to the graft length. For hybrid grafts, the elastic modulus measured parallel to the graft length was 2.0 (±0.4) MPa, having the combined mechanical property of both mesh and spun cast graft. Compared to natural artery which has an elastic modulus of a few MPa. (Abe H, Hayashi K, Sato M, Data book on mechanical properties of living cells, tissues and organs. Tokyo, New York: Springer; 1996), the hybrid grafts fabricated by electrospinning and spin casting techniques exhibit the mechanical property within the same range as the natural artery.

TABLE 1

Mechanical property of polyurethane grafts fabricated by electrospinning and spin casting techniques.

| Electrospun graft | Elastic Modulus (MPa) |
| --- | --- |
| Longitudinal | 0.43 (±0.04) |
| Transverse | 3.43 (±0.98) |
| Mesh | 1.25 (±0.28) |
| Spun cast graft | 4.34 (±0.05) |
| Hybrid graft | 2.00 (±0.40) |

Values are means±standard error of the mean. For electrospun grafts with anisotropic orientation of microfibers, elastic moduli were determined in both the longitudinal (orthogonal to aligned microfibers) as well as the transverse (parallel to aligned microfibers) directions to the graft length. Hybrid grafts were produced by the combined electrospinning and spin casting methods.

Alignment of Endothelial Monolayer

Figure 3:
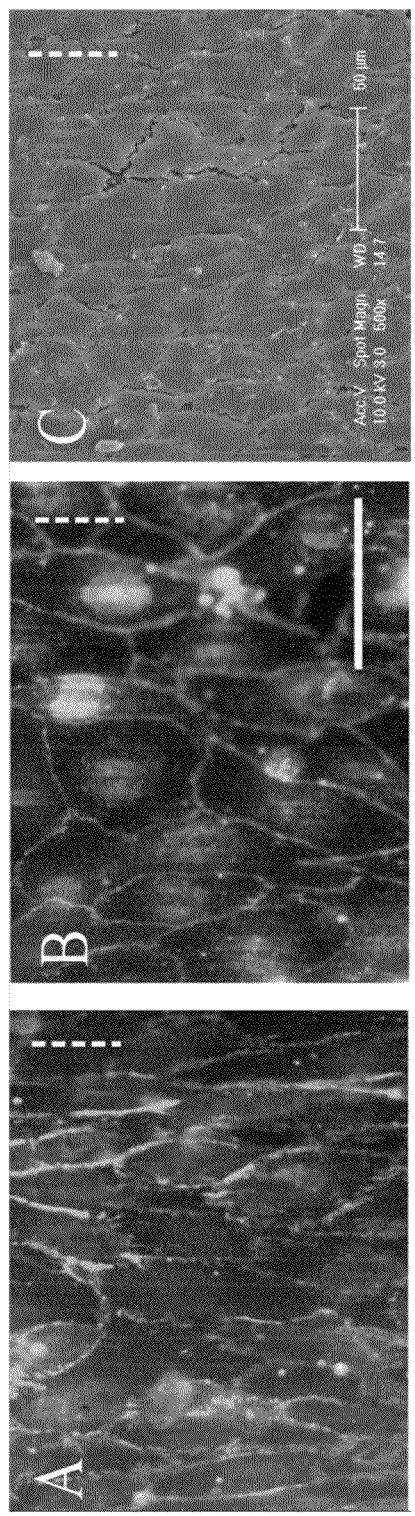
FIG. 3, comprising

Surface topography, both microchannels and microfibers, on the lumen of PU grafts provided a physical track to direct the alignment of endothelial cell shape parallel to the directions of channels and fibers, respectively. Using to cell seeding system comprising a syringe-based bioreactor and an orbital shaker, a uniform cell density on the graft lumen was obtained as visualized by fluorescently stained actin microfilament at 2 h, 3, 5 and 7 days (data not shown). For spun cast grafts, the monolayers of both BAECs and EA.hy926 endothelial cells maintained their alignment parallel to the channels on day 7 as shown by VE-cadherin staining and SEM images (FIG. 3). Besides the alignment of cell shape, cell nuclei also elongated and aligned in the direction of channels as observed by DAPI staining. The arrows in FIGS. 3A and 3B point at nuclei situated over a ridge and a channel, confirming that cells are not confined only within a ridge or a channel but rather conform over the topographic contour. This alignment of the endothelial monolayer emulates the naturally elongated endothelium directed by hemodynamic flow in linear arteries (Nerem et at, 1981 J Biomech Eng 103: 172-6).

Figure 4:
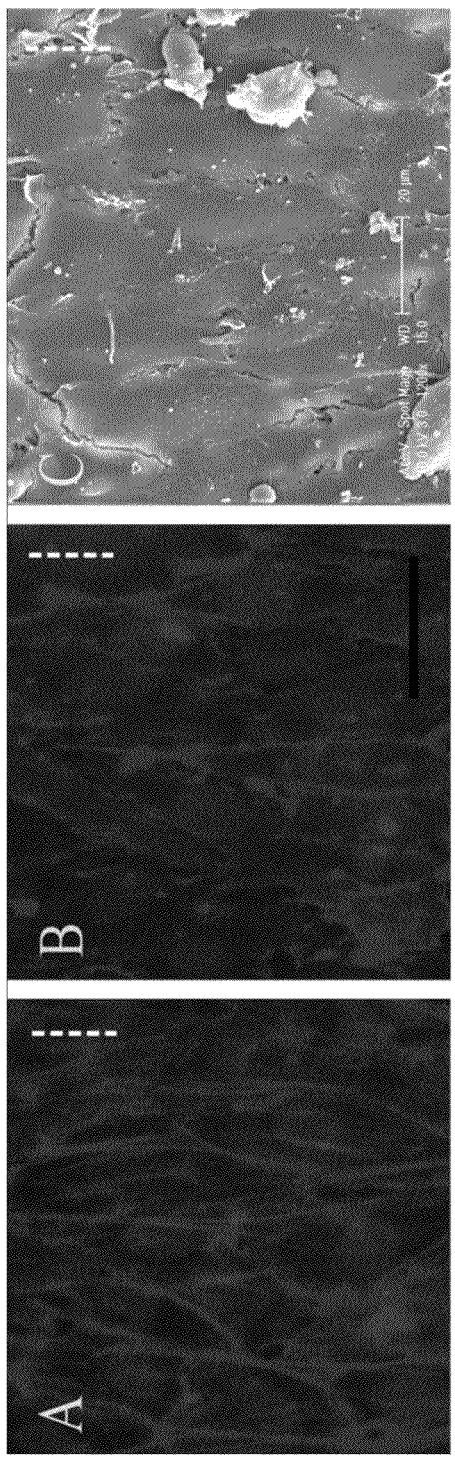
FIG. 4, comprising

Similarly to cell alignment parallel to microchannels, the monolayer of endothelial cells cultured on electrospun grafts also exhibited the alignment of cell shape parallel to the electrospun fibers (FIG. 4). The fluorescently stained actin microfilaments showed intense perimembrane actin outlining individual cell in the monolayer (FIGS. 4A and 4B). The uniform cell density was also observed by SEM (FIG. 4C) with cell shape aligned in the direction of microfibers. This alignment of endothelial cell shape guided by substrates' contact guidance is in agreements with previously studies on various cell types (Oakley et al., 1995 Cell Motil Cytoskeleton 31: 45-58; Jiang et at, 2002 Langmuir 18: 3273-3280; den Braber et at, 1996 Biomaterials 17; 2037-44; den Braber et al., 1998, J Biomed Mater Res 40: 291-300; Uttayarat et al., 2005 J Biomed Mater Res 75: 668-80; van Kooten et at, 1999 Tissue Eng 5: 223-40). Similar to the flow-induced elongated endothelium, the micro-scale surface topography directs the in vitro endothelial cell alignment without altering the cells' phenotype.

Endothelial Cells Maintained their function on Synthetic Polyurethane

Figure 5:
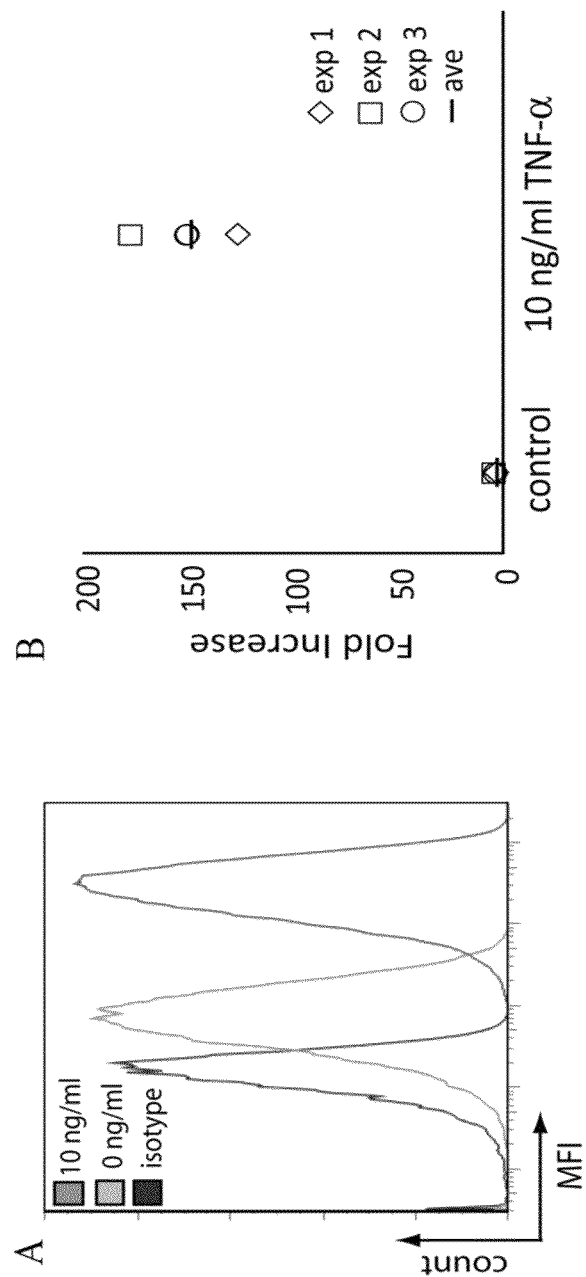
FIG. 5, comprising

To test whether endothelial cells cultured on synthetic surfaces are capable of maintaining their in vivo function, experiments were designed to evaluate the response of EA.hy926 endothelial cells to pro-inflammatory stimulus (e.g., TNF-α). This transformed cell line has been shown to interact with TNF-α but not LPS or 1L-β (Unger et al., 2002 Microvasc Res 64: 384-97) and the induced ICAM-1 expression was the only inflammatory adhesion molecule upregulated by TNF-α (Unger et. al., 2002 Microvasc Res 64: 384-97). Initial studies showed that the induced ICAM-1 expression saturated with TNF-α concentration beyond 10 ng/ml, in agreement with previous reports (Silverman et al., 1999 Am J Physio 277: C233-428). Cells were cultured on non-treated (without fibronectin), as-cast PU surfaces until 1 day post confluence. Alter incubation in 10 ng/ml TNF-α, for 16 h, the cells exhibited 44 and 151 fold increases in ICAM-1 expression compared to control (0 ng/ml TNF-α) and isotype (10 ng/ml TNF-α), respectively (FIG. 5). Therefore, it is believed that endothelial cells are not reactive to the chemical constituents of the graft and the cells maintain their response to the pro-inflammatory stimulus.

In addition to evaluating ICAM-1 expression, the attachment of monocyte to activated endothelial monolayer, an early step implicated in atherosclerosis lesion, was investigated. Cells were cultured on both non-treated PU substrates with smooth and microchanneled surfaces until 1 day post confluence, followed by incubation in medium containing 10 mg/ml TNF-α for 16 hours. When BBZ-labeled human monocytic U937 cells were introduced to the activated culture, there was an increase in the number of monocytes adhered on the activated (10 ng/ml TNF-α) endothelial monolayer, compared to control (0 ng/ml TNF-α) for both smooth and microchanneled PU surfaces. In addition, BBZ-labeled U937 cells were not observed to be present on bare smooth and microchanneled PU surfaces under the same incubation and washing conditions (data not shown). These results demonstrate that topographic textures on the surface of the graft did not elicit the inflammatory reaction of endothelial cells and inflammatory-induced cells underwent the injury process as shown in their adhesion to monocytes.

Non-Thrombogenic Grafts

Without wishing to be bound by any particular theory, it is believed that endothelialization of synthetic vascular grafts is a central approach in the development of non-thrombogenic, polymeric-based conduits. Despite the successful attachment of endothelial cells on various chemically modified synthetic grafts in vitro, the in viva transanastomic endothelial ingrowth into the midgraft area has not yet been achieved in clinical trials and animal models (Zilla et al., 2007 Biomaterials 28: 5009-27). This denuded portion of the graft can provoke the re-occurrence of thrombosis post implantation. In addition, the mismatch in mechanical property between synthetic graft and natural vascular tissue also initiates the subsequent thrombogenicity (Matsuda et al., 2005 J Biomed Mat Res 73: 125-31). The results presented herein demonstrate that surface topography can be generated onto the 3-D, small caliber polyurethane grafts such that the grafts can deliver topographic cue for endothelialization while maintaining the elastic property similar to that of the native artery.

Unlike porous surface, groove-like topography constituted by microchannels can induce the cellular alignment, recapitulating the in vivo elongated and aligned endothelium under hemodynamic flow (Utlayarat et al., 2005 Biomed Mater Res 75: 668-80; Nerem et al., 1981 J Biomech Eng 103: 172-6). The disclosure presented herein demonstrates that the spin casting technique on a slowly rotating mandrel enables a uniform transfer of micro-scale features from a 2-D polymer mold to a 3-D structure. This method can be applied to imprint various topographic textures on the lumen of artificial grafts. The results presented herein demonstrate that microchannels with dimensions smaller than the size scale of the cells promote directional guidance for cell migration that is parallel with the microchannels. Without pre-endothelialization, this directional tracks on 3-D synthetic grafts can promote endothelial cell migration from the native tissue into the grafts and improve cell attachment in the midgraft area.

Similar to the cell alignment parallel to microchannels, the alignment of endothelial cells on microfibers oriented helically along the graft length also confirms that the cells respond to a topographic feature of at least 1 μm in size. Without wishing to be bound by any particular theory, it is believe that this helical cell alignment can be useful for smooth muscle cells seeded underneath the endothelium (Stankus et al., 2006. Biomaterials 27(5):735-44). With intracellular actin microfilaments oriented helically on microfibers, the contractility of smooth muscle cells can additively enhance the grafts' elasticity in response to blood pressure acting normal to the graft lumen. Therefore, the architectural structure of cells seeded on the synthetic graft can be organized by micro-scale surface topography.

The combination of both electrospinning and spin casting techniques allow a novel fabrication of artificial grafts with different micro-scale structures to deliver specific cues and functions from the same polymeric material. Although PU has been extensively investigated as cardiovascular devices due to its superior mechanical property (Matsuda et al, 2005 J Biomed Mat Res 73: 125-31), the compliance of PU can vary with the architectural structure. The data presented herein demonstrate that PU with microfibrous structure has lowered elastic modulus than spun cast PU and more compatible to natural vascular tissue, about 2 MPa (Matsuda et al., 2005 J Biomed Mat Res 73: 125-31; Abe H, Hayashi K, Sato M. Data book on mechanical properties of living cells, tissues and organs. Tokyo, New York: Springer; 1996). Because the spin casting technique allows the PLY solution to completely fill all 3-D microchannels for the successful pattern transfer, the compliance of the spun east grafts can be restored by immediately electrospinning mesh of microfibers on the exterior of spun cast lumen. In contrast to the PCL-PU composite vascular graft (Williamson et al., 2006 Biomaterials 27: 3608-16), the hybrid PU gratis disclosed herein can be fabricated from the same polymeric material, thus conferring topographic cues for cellular alignment while maintaining the natural, compliant property of PU.

Modulation of ICAM-1 expression of endothelial cells grown on PU under physiological and pathological conditions indicates that the cells maintain their in vivo function on the artificial surface. The induction of the cells by TNF-α (10 ng/ml) significantly upregulated ICAM-1 expression and increased monocyte adhesion to the stimulated endothelial culture compared to the cells in their quiescent state (0 ng/ml TNF-α). This increase in adhesion of monocytes to vascular endothelium activates the subsequent leukocyte accumulation in atherogenesis (Silverman et al., 1999 Am J Physio 277; C233-42). The results presented herein agree with previous study that showed the increase in induced ICAM-1 expression and increased monocyte adhesion when EA.hy926 endothelial cells were treated with TNF-α. This endothelial property is specific to the transformed EA.hy926 cell line and can be inhibited by neutralizing CD11a and CD18 that promote the cell binding to lymphocytes (Brown et al., 1993 J Immunol Methods 163; 13-22). Therefore, endothelial cells cultured on an artificial PU surface of the invention remain in their quiescent state, similar to natural endothelium under physiological condition, and are capable of responding to inflammatory stimulus that provokes injury.

The results presented herein demonstrate that the 3-D small caliber polyurethane grafts fabricated by the methods of the invention comprising electrospinning and spin casting techniques, have a well-defined topographic microchannel feature that is preferably ≤5 μm wide and is compliant compatible with native vascular tissue. The topographic microchannels and microfibers effectively induced the alignment of endothelial cells and intracellular actin microfilaments in the direction of channels and fibers. The compliance of grafts with microchannels on the lumen can be restored by incorporating mesh of electrospun fiber on the exterior. At confluence, the aligned endothelial cells were positively immunostained for VE-cadherin. The expression of ICAM-1 upon activation with TNF-α confirmed that the cells on synthetic polyurethane retained their in vivo function. The synthetic grafts of the invention can be readily made by electrospinning and spin casting techniques to deliver specific cues while allowing the cells to maintain their endothelial property.

Example 2

Solvent Effects on Polyurethane Fibers

Tissue-engineered scaffolds with various morphological structures can be fabricated by electrospinning to emulate the natural assembly of extracellular matrix (ECM) proteins, similar to that in the native tissue. The nature of electrospun polyurethane (Hi) fibers depend on the solubility of PU in different organic solvents. To compare three different solvents, dimethylformamide (DMF), tetrahydrofuran (THF), and hexafluoro-2-propanol (HFP), the experiments disclosed herein were designed to optimize the formation of uniform electrospun PU microfibers with mechanical properties in the range of natural vascular vessels.

The results presented herein demonstrate that electrospun fibers from HFP exhibited uniform, bead-free and continuous fibers of ~1-μm diameter, whereas fibers derived from THF- and DMF exhibited varicosities along the fiber length as visualized by electron microscopy. When assembled into grafts with microfibers helically oriented along the graft's longitudinal axis, the transverse compliance was about eight fold higher than the longitudinal compliance. The grafts could be strained, without failure, longitudinally up to 300% with the microfibers realigning their orientation with applied tensile load. Endothelial cells formed confluent monolayers on all PU scaffolds irrespective of fiber morphology, though cellular alignment was achieved only on oriented microfibers.

This favorable compliance as well as micro-scale directional track endorsed synthetic vascular grafts with multiple functions as natural ECM scaffold.

The materials and methods employed in these experiments are now described.

Electrospinning of Polyurethane

The fabrication of polyurethane meshes and grafts by electrospinning included the preparation of the polyurethane solutions and the electrospinning setup. Tecothane, an aromatic polyether polyurethane, was obtained from Thermedies Inc. (Woburn, Mass.), purified, and characterized as previously reported (Stachelek et al., 2005 J Biomed Mater Res A 72(2)200-12). Based on previous reports (Courtney et al., 2006, Biomaterials 27(19):3631-3638; Sidouni et al., 2001, Surface Science 491:355-369; Stachelek et al., 2005 J Biomed Mater Res A 72(2):200-12; Stankus et al., 2004, J Biomed Mater Res A. 70(4):603-14), N,N-dimethylformamide (DMF), tetrahydrofuran (THF) and 1,1,1,3,3,3-hexafluoro-2-propanol (HFP) were selected as candidate solvents to prepare PU solutions. Freeze-dried polyurethane was dissolved in DMF, THF at concentrations of 7%, 8.5% and 10% and HFP at concentrations of 1%, 3%, 4% and 5% under stirring for 2 h at 40° C. Subsequently, the solutions were left stirring at room temperature overnight to ensure that the PU was completely dissolved. Due to the suspension of PU in DMF at room temperature, DMF-based solution was reheated to 60° C., prior to electrospinning.

A horizontal electrospinning station was setup inside a chemical hood as previously described (Li et al., 2006, J Biomed Mater Res A, 79(4):963-73). To fabricate small diameter grafts, mandrels with 4-mm diameter custom imide from aluminum rods were used. For electrospinning, the power supply (ES30-0.1P, Gamma High Voltage Research) was set to 12 kV to drive jets of electrospun PU fibers across a distance of 12 on between the source and the target. The PU solutions were fed at 0.8 ml/h by a syringe pump (KD Scientific infusion Pump. Fisher) through a blunt 18 gauge needle towards either a glass cover slip (15-mm diameter for generating random fibers and thicker electrospun sheets) or the mandrel rotating at 35,000 rpm (Dremel) for generating small diameter grafts. For electrospun graft, all grafts were dried overnight under laminar flow inside the chemical hood before being released from the mandrel.

Mechanical Testing

To determine the elastic, moduli using Instron (model 5564 with the Merlin version 9.0 software), PU samples in both mesh/sheet and graft geometry were cut into a rectangular shape with the dimension approximately 0.2 mm×5 mm×50 mm (thickness×width×length). Due to the helical organization of electrospun fibers about the tubular graft's long axis, the elastic modulus of individual grafts was characterized along the longitudinal (perpendicular to aligned fibers) as well as the transverse (parallel to aligned fibers) directions. Each sample was strained to 50% of its original length at a rate of 5 min/min with a maximum load transducer set at 0.2 N. After ten cycles of 50% strains, the sample was then allowed to strain to 300%. Data were recorded as load and displacement. About 3 to 5 samples of mesh/sheet and grafts from each of the different solvent conditions were tested.

Cell Culture and Cell Seeding

The immortalized human umbilical vein endothelial cell line EA.hy926 were routinely maintained in DMEM with 4.5 g/L glucose supplemented with 10% FBS and 0.5% penicillin streptomycin (25 IU/mL penicillin and 25 µg/mL streptomycin) at 37° C. in a 5% $CO_2$ incubator. Cell passages 35-45 were used in the experiments.

For sterilization, all PU samples were immersed in a solution containing 1% (v/v) of stock streptomycin, penicillin and amphotericin (Mediatech) in tissue culture grade water for three days. The samples were then placed inside 12-well tissue culture plates (VWR) for cell seeding. EA.hy926 cells were seeded at a density of 500,000 cells per sample. After the cells reached confluence, the samples were fixed in 4% formaldehyde for 15 min at room temperature. The cells were then permeabilized in 0.1% Triton-X for 3 min, followed by rinsing in PBS, and then incubated in a PBS solution containing 2 µg/ml Hoechst 33258 (BBZ, nuclear stain, Sigma) and 1 µg/ml tetramethylrhodamine B isothiocyanate-phalloidin (RITC-phalloidin, F-actin stain, Sigma) for 20 min at room temperature. After three washes in PBS, the PU samples were mounted on glass microscope slides for visualization by fluorescence microscope (Leica DMRX).

Scanning Electron Microscopy Analysis

To observe the ultrastructure of electrospun Pt; fibers, the samples were sputter coated with platinum and examined by scanning electron microscope (FEI XL30, Drexel University) at acceleration voltages of 5 and 10 kV and 15 mm working distance. To visualize the luminal surface of 3-D grafts, the samples were cut longitudinally with the exterior mounted onto the sample stubs. About 5-8 images were acquired for each sample.

Statistical Analysis

All data are expressed as mean±standard deviation. Statistical analysis was performed by one-way ANOVA, followed by post-hoc Student's t-test with $p \leq 0.05$ being statistically significance.

The results of the experiments are now described.

Solvent Effect on the Morphology of Electrospun PU Fibers

Figure 6:
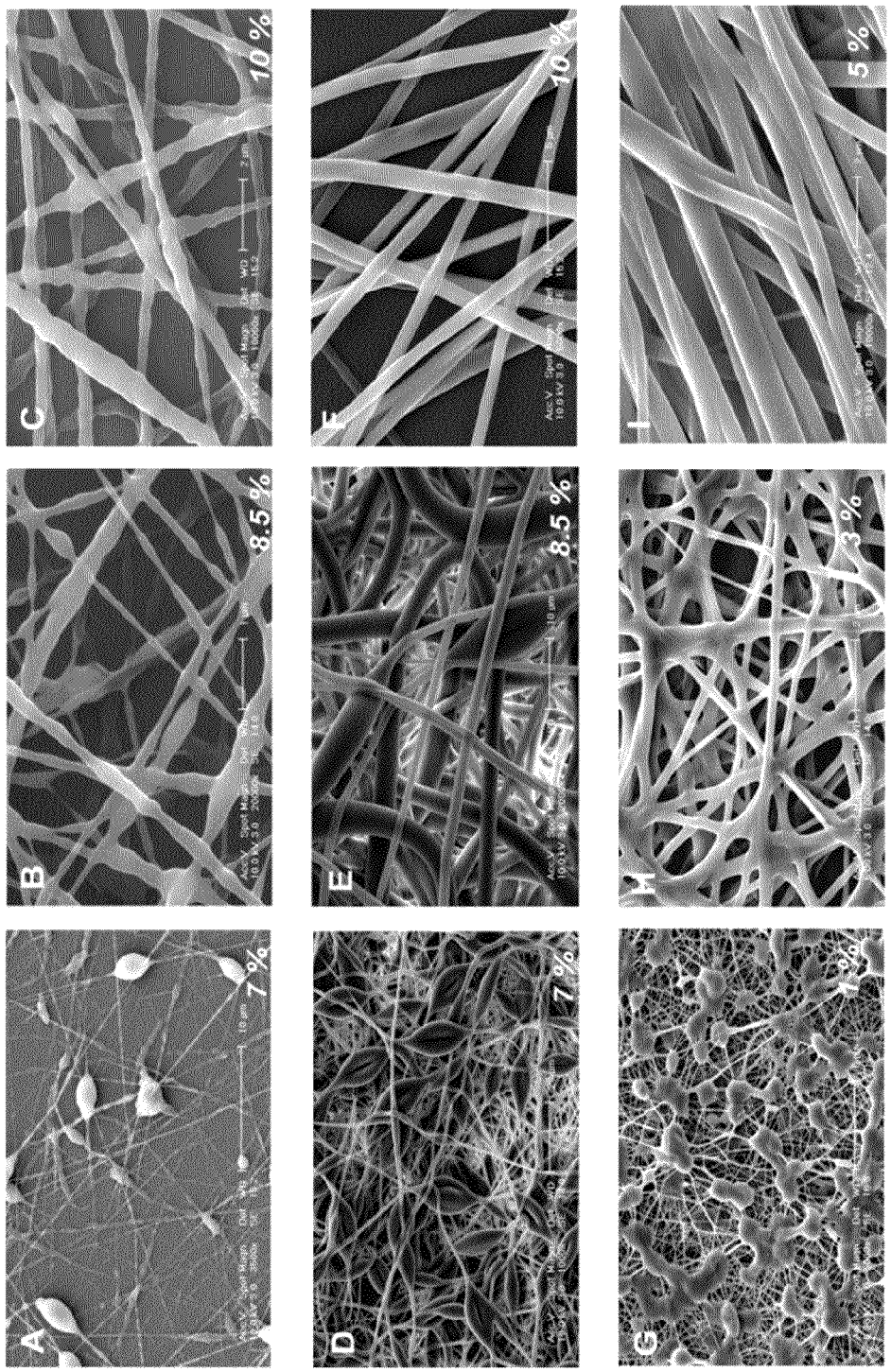
FIG. 6, comprising

On static cover slip targets, electrospun PU fibers formed a woven mesh/sheet with varied fiber morphology due to differences in the solubility of PU in the three organic solvents examined. FIG. 6 shows the resulting morphologies of PU fibers electrospun from the three different solvents. At 7% PU in DMF (FIG. 6A), micro-scale irregularities (pearl-like beads) disrupted the fiber continuity; these pearl-shaped beads disappeared at higher PU concentrations. In the absence of these larger-scales pearl-like beads, smaller kinks persisted along the fiber at 8.5% and 10% PU in DMF (FIGS. 6B and 6C), preventing the fiber surface to be completely smooth. In addition, it was observed over time during electrospinning at room temperature, that PU precipitated out of DMF at all concentrations tested. For fibers electrospun from THF-based solution, elipsoid doughnut-shaped beads formed along the fibers in contrast to those prepared in DMF. Traces of fiber separation were also observed on these beads. The formation of these doughnut-shaped beads decreased with increasing PU concentrations from 7% to 10% (FIGS. 6D to 6F). At the highest PU concentration tested, the fibers were uniform in size, about 2.64 (±0.59) µm in diameter, and possessed relatively smooth surface compared to fibers electrospun from DMF.

In contrast to DMF and THF, using TH as a solvent required much lower concentrations of PU to achieve uniform fibers without any irregularity. The formation of circular clumps along the fibers was observed at 1% PU in HFP (FIG. 6G) but disappeared when the concentration of PU was raised to 3% (FIG. 6H). At this 3% PU concentration, microfibers formed an interconnected network with junctions where the fibers merged together. At 5% PU in HFP, the fibers were completely smooth and uniform in size, about 1.20 (±0.31) µm in diameter. Table 2 shows the effect of PU concentration in THF and HFP solvents on the size of electrospun fibers. Without wishing to be bound by any particular theory, it is believed that that the complete dispersion or our PU in THF or HFP contributes to the formation of uniform and continuous microfibers forming non-woven mesh/slicer, the thickness of which can be controlled by the duration of the electrospinning procedure.

TABLE 2

Effect of polyurethane concentration in THF and HFP solvents on the size of electrospun microfibers.

| Solvents | % PU | Fiber Diameter (µm) |
|---|---|---|
| THF | 7 | 0.80 (±0.22) |
| | 8.5 | 1.68 (±0.56) |
| | 10 | 2.64 (±0.59) |
| HFP | 3 | 0.33 (±0.07) |
| | 4 | 0.44 (±0.10) |
| | 5 | 1.20 (±0.31) |

Electrospun Small Diameter PU Grafts

Figure 7:
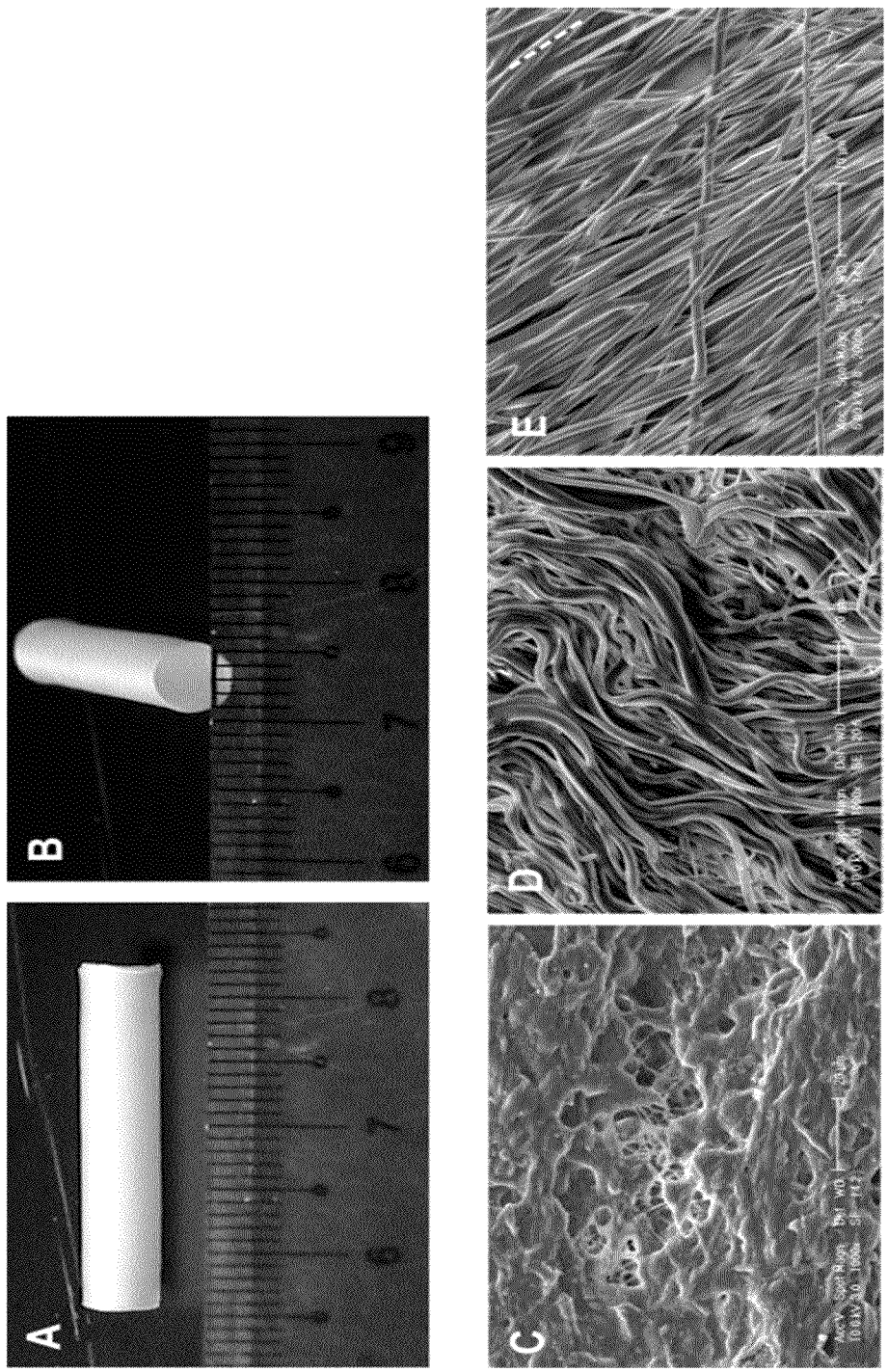
FIG. 7, comprising

Electrospun fibers collected on a high-speed rotating mandrel formed 3-D tubes with fibers helically aligned about the tube's longitudinal axis. Based on the formation of continuous electrospun fibers in the non-woven mesh, solutions of 10% PU in DMF, 10% PU in THF and 5% PU in HFP were prepared for electrospinning of PU grafts. FIGS. 7A and 7B show the side and transverse views of a small diameter graft electrospun from 5% PU solution in HFP, with a length and diameter of 38 mm and 4 mm, respectively.

Scanning electron microscopic examination revealed a loss of fiber morphology in the lumen of grafts fabricated from 10% PU in DMF (FIG. 7C). During the spinning process, individual fibers merged to form a rough surface topography. In contrast, grafts electrospun from 10% PU in THF retained the morphology of microfibers on the graft lumen (FIG. 7D). Although the fiber morphology was preserved, PU solution in THF was more viscous than PU solutions prepared in DMF and HFP, which hindered the feasibility of the electrospinning process. Similar to the THF, the continuous and uniform fiber morphology was also observed on the lumen of grafts electrospun from 5% HIT (FIG. 7E). Most of these fibers were oriented helically about the long axis of the graft. This alignment of microfibers was less evident in graft fabricated from the THF system. Without wishing to be bound by any particular theory, it is believed that electrospinning of PU from HFP allows for optimal formation of small diameter grafts with uniformly oriented fibers transverse to the longitudinal graft axis.

Mechanical Property of Electrospun PU Mesh and PU Grafts

To determine the tensile mechanical properties of electrospun mesh/sheets and grafts comprised of continuous microscale fibers, PU samples were tested using Instron. Table 3 shows the elastic moduli of all samples when subjected to 50% strain. In the woven mesh/sheet geometry, the elastic moduli of PU electrospun from either THF and HFP were very similar around 1.25-1.4 MPa. Unlike sheets, PU grafts electrospun from HFP-based solution exhibited anisotropic moduli within the same sample due to the orientation of microfibers. In the longitudinal direction (orthogonal to the aligned fibers), the elastic modulus was 0.43 (±0.04) MPa, whereas it increased eightfold to 3.43 (±0.98) MPa in the transverse direction (parallel to the aligned fibers). Similar results were obtained from PU mesh and PU graft fabricated from THE-based solution (Table 3).

TABLE 3

Elastic moduli (E) of electrospun PU in two selected solvents: HFP, THF measured by Instron under the tensile mode (maximum load transducer = 0.1N and cross-head speed = 5 mm/min) up to 50% strain for 10 cycles.

| Solvents | Graft Longitudinal | Graft Transverse | Mesh |
|---|---|---|---|
| HFP | 0.43 (±0.04) | 3.43 (±0.98) | 1.25 (±0.28) |
| THF | 0.46 (±0.04) | 4.63 (±0.32) | 1.41 (±0.03) |

Figure 8:
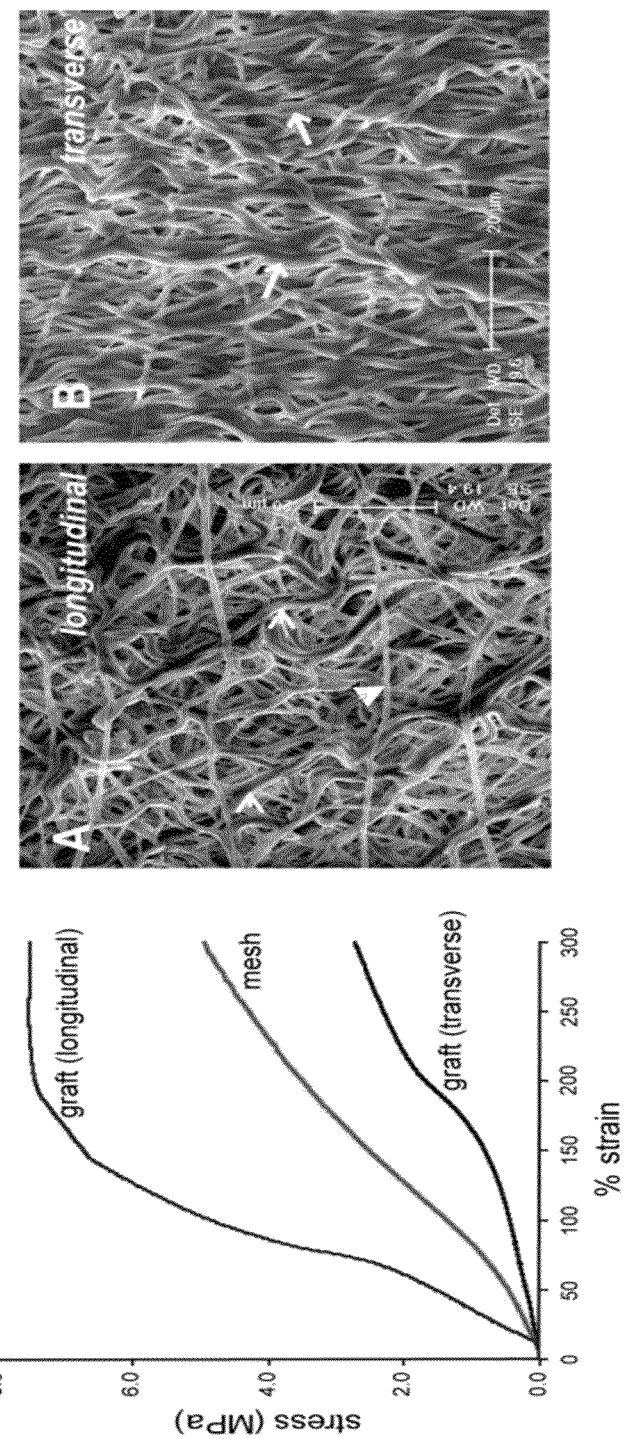
FIG. 8, comprising

Different mechanical behaviors were observed on the stress-strain curves due to the organization of electrospun microfibers. FIG. 8 shows representative stress-strain curves of a representative PU mesh and a graft prepared from a 5% PU solution in HFP as well as the corresponding SEM images of the graft visualized after tensile testing. The slope of the PU mesh was linear throughout 300% strain, whereas there was a change in the graft's stress-strain curves. For grafts with tensile stress applied in the longitudinal direction (perpendicular to the aligned microfibers), a reflection occurred on the curve at about 150% strain with a slight increase in the slope. The SEM image (FIG. 8B) showed that the aligned microfibers became randomly organized after the removal of the tensile stress. A few microfibers (solid arrow head) remained helically oriented transverse to the graft, whereas most fibers were randomly organized or in the process of realigning in the direction of load (open arrow heads). By contrast, when the tensile stress was applied in the transverse direction (parallel to aligned microfibers) the pre aligned microfibers (see FIG. 7E) formed bundles (solid arrows, FIG. 8C) while maintaining their alignment parallel to the applied tensile stress. Among the three curves in the linear region, the slope of the graft with microfibers aligned in the direction of tensile stress was the steepest before it reached a plateau at about 200% strain. The results presented herein demonstrate that both mesh and aligned fibers (parallel or perpendicular to load) can be deformed to 300% strain without failure and their diverse mechanical behaviors become pronounced beyond 100% strain.

Cell Proliferation on PU Mesh and PU Graft

The cytocompatibility of artificial PU scaffolds was assessed by evaluating the capability of endothelial cells to form histiotypic monolayers on the various materials. As seen in FIGS. 9A-9C, after seeding and 5 days in culture, the cells formed monolayers on all PU mesh samples irrespective of different surface topographies of smooth or disrupted microfibers. Grafts electrospun from 5% PU solution in HFP was selected for studying endothelial cell interactions with the PU.

After isotropic seeding inside the graft and 14 days in culture, EA.hy926 reached confluence on uniformly along the entire lumen of the graft. Individual cells in the monolayer maintained their alignment parallel to the oriented microfibers (FIG. 9E), whereas a "cobblestone-like" monolayer was observed on PU meshes (FIGS. 9A-C). This oriented cellular alignment agreed with previous studies that showed the alignment of cell shape by groove-like or fibrillar surface topographies (Britland et al., 1996, Exp Cell Res 228(2)313-25; den Braber et al, 1998, J Biomed Mater Res 40291-300; Oakley et al, 1995, Cell Motil Cytoskeleton. 31(1)45-58; Uttayarat et al., 2005, J Biomed Mater Res 75(3):668-80). Without wishing to be bound by any particular theory, it is believed that the PU scaffolds fabricated by electrospinning support endothelial cells proliferation and only oriented microfibers can direct cell alignment parallel to the direction of the fibers.

Multifunctional Synthetic Vascular Grafts

Electrospinning provides a new, rapidly expanding platform technique to fabricate cardiovascular prostheses with compliances compatible to those of natural cardiovascular tissue. Anisotropy in the prostheses' mechanical property can be maneuvered by the organization of constitutive electrospun microfibers, allowing these prostheses to emulate the complex mechanical properties of the native tissue. In addition to strengthening the scaffold's structural property, these microfibers also provide contact guidance to direct cellular alignment.

Electrospun microfibers of the non-woven mesh are physically entangled. Thus to prevent the mesh from tearing under tensile stress, helically oriented microfibers can rearrange their alignment to support the graft under tensile loading (FIG. 8). The realignment of helically oriented microfibers parallel to the graft's longitudinal axis can contribute to the change in slope of stress-strain curve (FIG. 8 and Table 3). This transition in the reorganization of fibril constituents is analogous to arrangement of the predominant ECM molecules in collagen-rich tissue such as tendon (Gutsmann et al., 2004 Biophys J 86: 3186-3193), in which the tissue enters a linear region (linear increase in stress with increasing strain) when collagen fibers stretch to uncoil kinks at lower strain (<10%). At higher deformation (>15% strain), the collagen-rich tissue enters a creep region as the fibers slide past each other (Gutsmann et al., 2004 Biophys J 86: 3186-3193), resulting in the leveling of stress at high strain before rupture. Without wishing to be bound by any particular theory, it is believed that creep deformation may explain the result presented here (FIG. 8) in which stress reaches the plateau at 200% strain when tensile stress was applied transverse to the graft (parallel to aligned microfibers). Despite creep deformation, the results presented herein suggest that microfibers can realign their orientation with the load to maintain the graft's structural integrity. Thus, the organization of fibril constituents, either in woven mesh or aligned microfibers transverse to the graft's longitudinal axis, can enhance the graft's mechanical property to withstand tearing and rupture. This notion is of particular importance for engineering natural or biohybrid vascular grafts for the arterial circulation, in which these grafts must be able to with stand pressures exceeding 200 mm Hg.

To generate uniform and continuous PU microfibers, the solubility of PU in organic solvent becomes an important parameter in electrospinning. Although PU is typically dissolved in organic solvents such as DMF and THF, the resulting electrospun PU microfibers fabricated from these two solvents exhibited irregularities (e.g., beads and varicosities; FIG. 6). In DMF, the resuspension of the tested PU at room temperature may have contributed to the formation of irregular clumps, whereas in both THF and HFP at low PU concentrations and with the set spinning parameters, solvent evaporation was incomplete and interfered in part with the formation of fibers, causing the solvent droplets to be deposited along the formation the microfibers. Although the increase in PU concentration in both HFP (5%) and THF (10%) prevents the formation of these clumps, the rise in viscosity of THF-based solution impedes the fabrication processing.

When using a high-speed rotating mandrel as target, the high boiling point of DMF, 153° C. (Lide D. Handbook of Chemistry and Physics 88th Edition, Boca Raton, Fla.; CRC Press/Taylor and Francis Group, LLC; 2008, p. 6-63), hinders solvent evaporation, compared to much lower boiling points of THF, 65° C. (Lide D. Handbook of Chemistry and Physics 88th Edition. Boca Raton, Fla.: CRC Press/Taylor and Francis Group, LLC; 2008, p. 6-63.), and HIT, 59° C., at the same vapor pressure. Thus, DMF trapped within the layers of PU microfibers may contribute to Fibers merging into a film-like morphology (FIG. 7C). In the PU system discussed herein, HFP has shown to be the optimal solvent for electrospinning uniform microfibers in both mesh and graft geometry.

Figure 9:
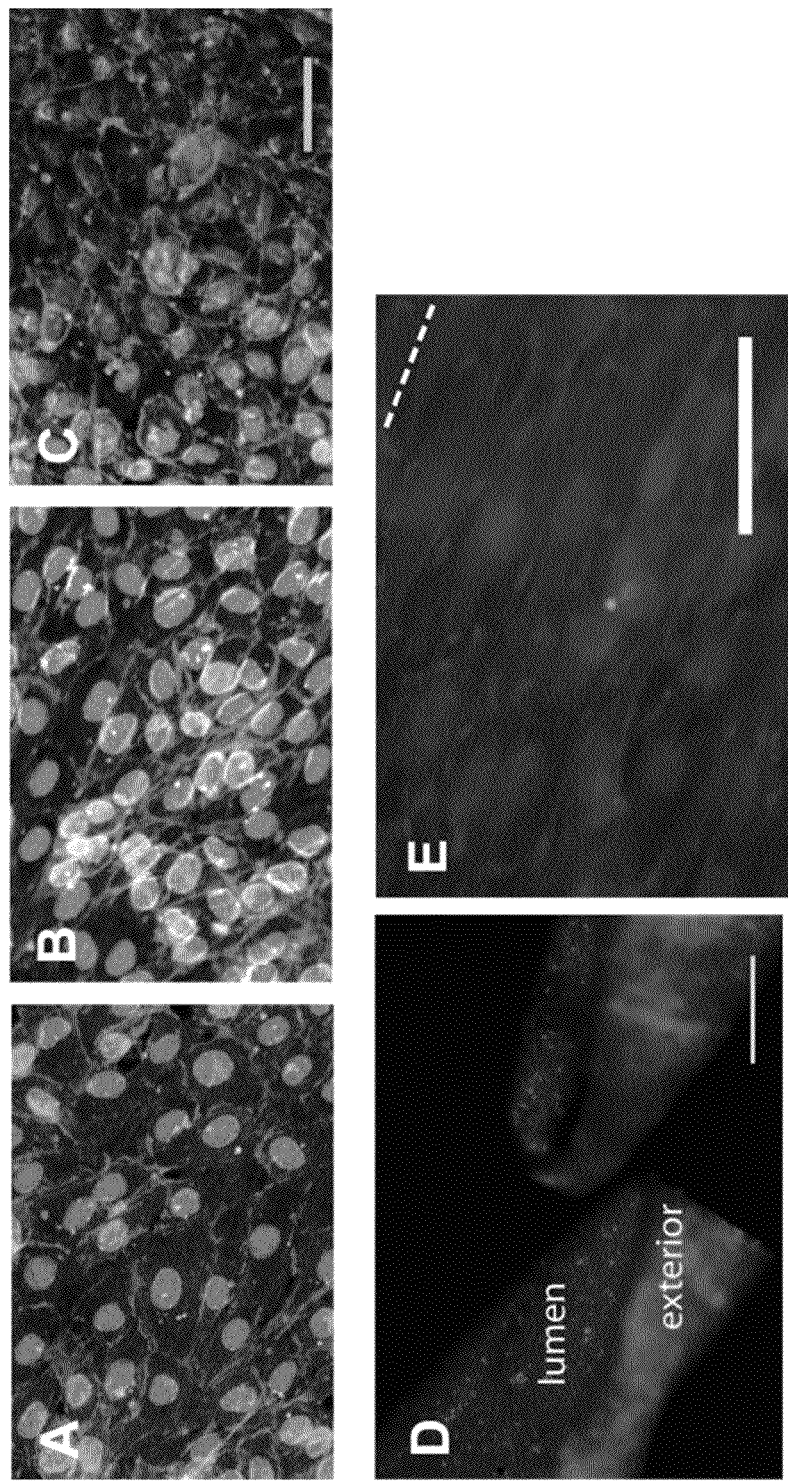
FIG. 9, comprising

While the organization of aligned microfibers provides for the anisotropic elasticity of the electrospun PU, the surface topography of the aligned fibers also guides cell orientation as assessed by directional reorganization of cells in monolayers growing on the aligned fibers vs. the random mesh (FIG. 9). Endothelial cells have been shown to align parallel to arrays of well-defined, micro-scale grooves (Uttayarat et al., 2005, J Biomed Mater Res 75(3); 668-80), sinusoidal waves (Jiang et al., 2002. Langmuir 18:3273-3280), as well as a mix of aligned poly(caprolactone) fibers (200 nm to 1 µm in fiber diameter) (Ma et al, 2005. Tissue Eng 11(7-8):1149-58). Although the diameter of the PU microfilm's spun out of 5% HPP is approximately 1.20 (±0.31) µm, the thickness of these microfilm's exposed to the cells are less than the actual fiber diameter due to winding and layering of these microfibers (FIG. 7E). Since the microfibers are uniform in size, the results presented herein ascertain that the fiber size of at least 1 µm can effectively guide cell alignment parallel to the direction of fibers.

Both the lumen (FIG. 9) and the exterior (not shown) of graft provide surfaces for cell attachment spreading and cell proliferation. Hence, different cell types can be seeded on both sides of the graft to improve the graft's functions. While the fabrication of cell-based "natural" grafts might hike up to 9 months to complete all the three vascular tissue layers (L+Heureux et al., 1998, FASEB 12(1)47-56), differential seeding of both sides of the hybrid grafts of the invention with endothelial cells and smooth muscle cells, which can be completed in only a few days, strengthens the mechanical and biocompatible properties of the non-degradable, compliant graft. The presence of circumferentially aligned smooth muscle cells on the graft exterior can enhance the radial contractility in response to pulsatile arterial flow, while the endothelial cell monolayer can restore the non-thrombogenicity of the graft lumen.

The results presented herein demonstrate the successful Fabrication of smaller diameter vascular graft by electrospinning. Among three solvents tested, polyurethane solution prepared in HFP yielded smooth, continuous electrospun microfibers with fiber diameter of about 1 µm. On a static collector, these electrospun fibers formed a mesh consisting of randomly entangled fibers, whereas on a high-speed rotating mandrel the fibers formed a 3-dimensional graft with microliters oriented helically along the mandrel. In terms of mechanical properties, the PU mesh exhibited isotropic elastic modulus in the range of natural vascular tissue. For polyurethane tubes, higher elastic moduli were obtained in the direction parallel to aligned microfibers, while the graft maintained its structural integrity when tension was applied perpendicular to these fibers up to 300% strain. For cell culture, aligned microfibers on the graft lumen induced endothelial cell alignment parallel to the fibers and this cell alignment was maintained at confluence. Without wishing to be bound by any particular theory, it is believed that optimized electrospinning of polyurethane provides a reliable platform technology for engineering of small diameter vascular graft with good mechanical properties and a textured surface topography suitable for guiding cellular alignment.

The disclosures of each and every patent, patent application, and publication cited herein are hereby incorporated herein by reference in their entirety.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

The invention claimed is:

1. A hybrid graft comprising an exterior surface and a luminal surface, wherein the luminal surface comprises a first polymer with a micropattern of grooves to which cells adhere and orient along, and wherein the exterior surface comprises a second polymer electrospun on the first polymer, wherein the second polymer provides mechanical properties to the first polymer, wherein each groove has a depth of about 1 µm, a width of about 5 µm and is positioned 5 µm apart from each other.

2. The hybrid graft of claim 1, produced using a hybrid method, wherein the method comprises a combination of a first electrocasting/electrospraying methodology to produce a micropatterned surface on the luminal surface and a second electrospinning methodology to produce electrospun fibers on the exterior surface.

3. The hybrid graft of claim 1, wherein the cells are selected from the group consisting of chondroblasts, chondrocytes, fibroblasts, endothelial cells, osteoblasts, osteocytes, epithelial cells, epidermal cells, mesenchymal cells, hematopoietic cells, nerve cells, Schwann cells, glial cells, stem cells, dorsal cool ganglia, and combinations thereof.

4. The hybrid graft of claim 1, wherein the hybrid graft is a vascular graft.

5. The hybrid graft of claim 1, wherein the luminal surface comprises a polymeric material selected from the group consisting of poly-(D,L-lactide-co-glycolide) (PLGA), poly-(dimethylsiloxane) (PDMS), poly-(l,lactide-co-caprolactone-co-glycolide) (PLCG) polycaprolactone (PCL), polylactic acid (PLA), polystyrene, polyurethane, polytetrafluoroethylene (ePTFE), and tetraphthlate (Dacron).

6. The hybrid graft of claim 1, wherein the luminal surface comprises cholesterol modified polyurethane.

7. The hybrid graft of claim 1, wherein the luminal surface and exterior surface comprise cholesterol modified polyurethane.

8. The hybrid graft of claim 1, where the hybrid graft promotes endothelialization and is non-thrombogenic.

* * * * *